(12) United States Patent
Haudenschild et al.

(10) Patent No.: US 6,401,072 B1
(45) Date of Patent: *Jun. 4, 2002

(54) CLINICAL CRITICAL CARE PATH SYSTEM AND METHOD OF USING SAME

(75) Inventors: Chris A. Haudenschild, La Jolla; Jean Francois Lancelot; Kristopher S. Urquhart, both of San Diego, all of CA (US)

(73) Assignee: Clini Comp International, Inc., San Diego, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/977,522

(22) Filed: Nov. 24, 1997

Related U.S. Application Data

(63) Continuation of application No. 08/396,004, filed on Feb. 28, 1995, now abandoned.

(51) Int. Cl.[7] .............................................. G06F 17/60
(52) U.S. Cl. ......................................................... 705/3
(58) Field of Search ............................. 705/2, 3; 707/1, 707/10, 100, 200, 205

(56) References Cited

U.S. PATENT DOCUMENTS

| | | | |
|---|---|---|---|
| 4,878,175 A | * 10/1989 | Norden-Paul | 705/3 |
| 5,018,067 A | 5/1991 | Mohlenbrock et al. | 364/413.02 |
| 5,301,105 A | 4/1994 | Cummings | 364/401 |
| 5,583,758 A | * 12/1996 | McIlroy | 705/3 |
| 5,655,084 A | * 8/1997 | Pinsky et al. | 705/3 |
| 5,850,221 A | * 12/1998 | Macrae et al. | 345/348 |

FOREIGN PATENT DOCUMENTS

WO    WO 97/15021    *  4/1997

OTHER PUBLICATIONS

Tanaka, H, "Information Engineering and its application to medical treatment", Journal of the Institute of Electrical Engineers of Japan, vol. 111, No. 5, p390–3, Dialog file 2, accession No. 04109490, 1991.*

* cited by examiner

*Primary Examiner*—Frantzy Poinvil
(74) *Attorney, Agent, or Firm*—Foley & Lardner; Bernard L. Kleinke

(57) ABSTRACT

A new and improved clinical critical care path system, which can be tailored readily for a given patient diagnosis for either single or combined medical and/or surgical diagnoses. The clinical information system stores critical care information for various patient diagnoses and retrieves them for a given patient. Treatment information is tailored to a given patient by enabling selected treatment information to be edited. Where multiple diagnoses are present, the prescribed or ordered treatment plans for each diagnosis are merged for a given patient, and potential conflicts are determined for any ordered activity. Upon determination of a conflict, patient treatment information is repeated on separate display lines to alert the healthcare provider to permit the healthcare provider to analyze the conflict and to determine what order or orders should be entered. Customized multiple diagnosis treatment information can then be entered and stored for a given patient.

38 Claims, 27 Drawing Sheets

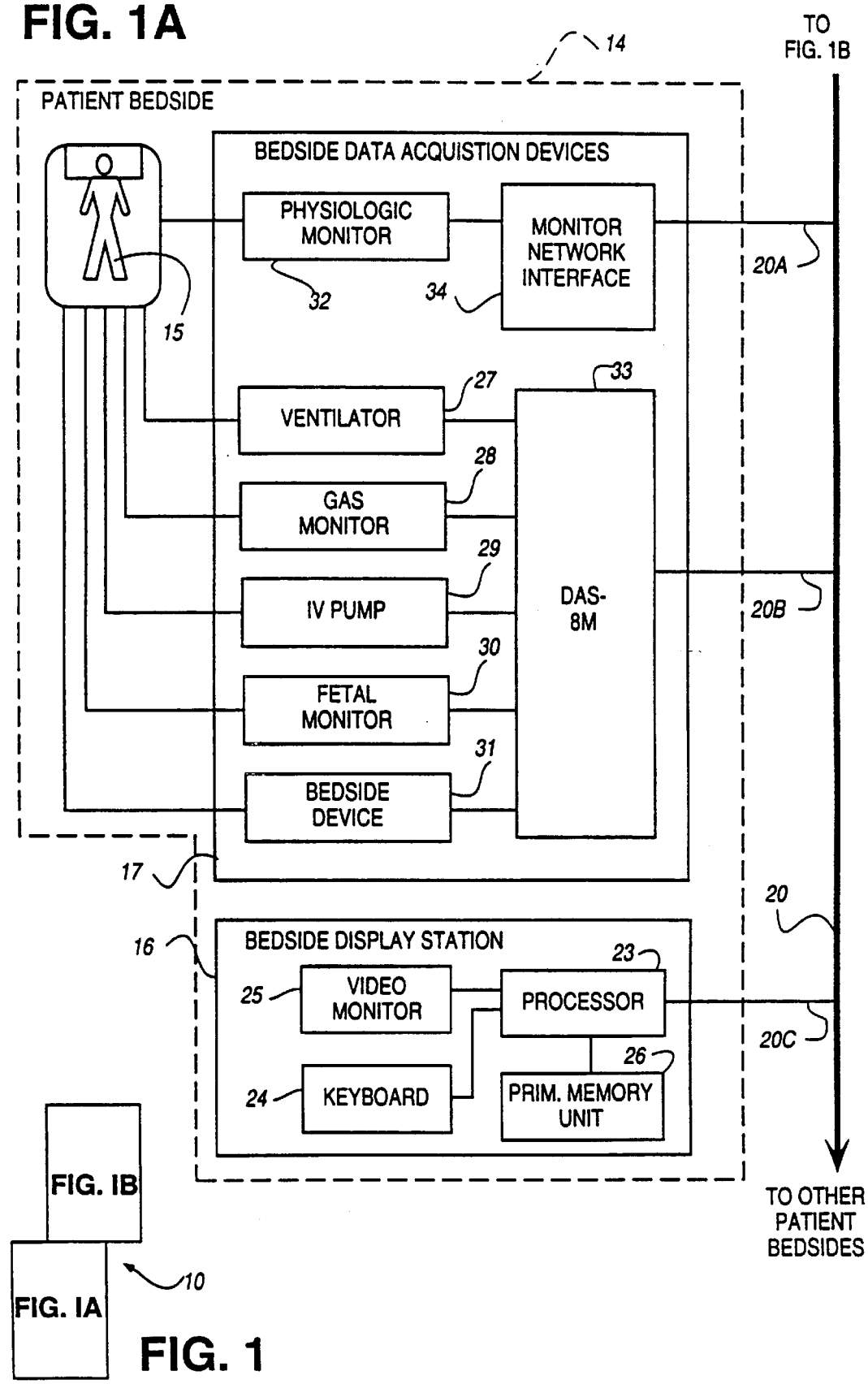

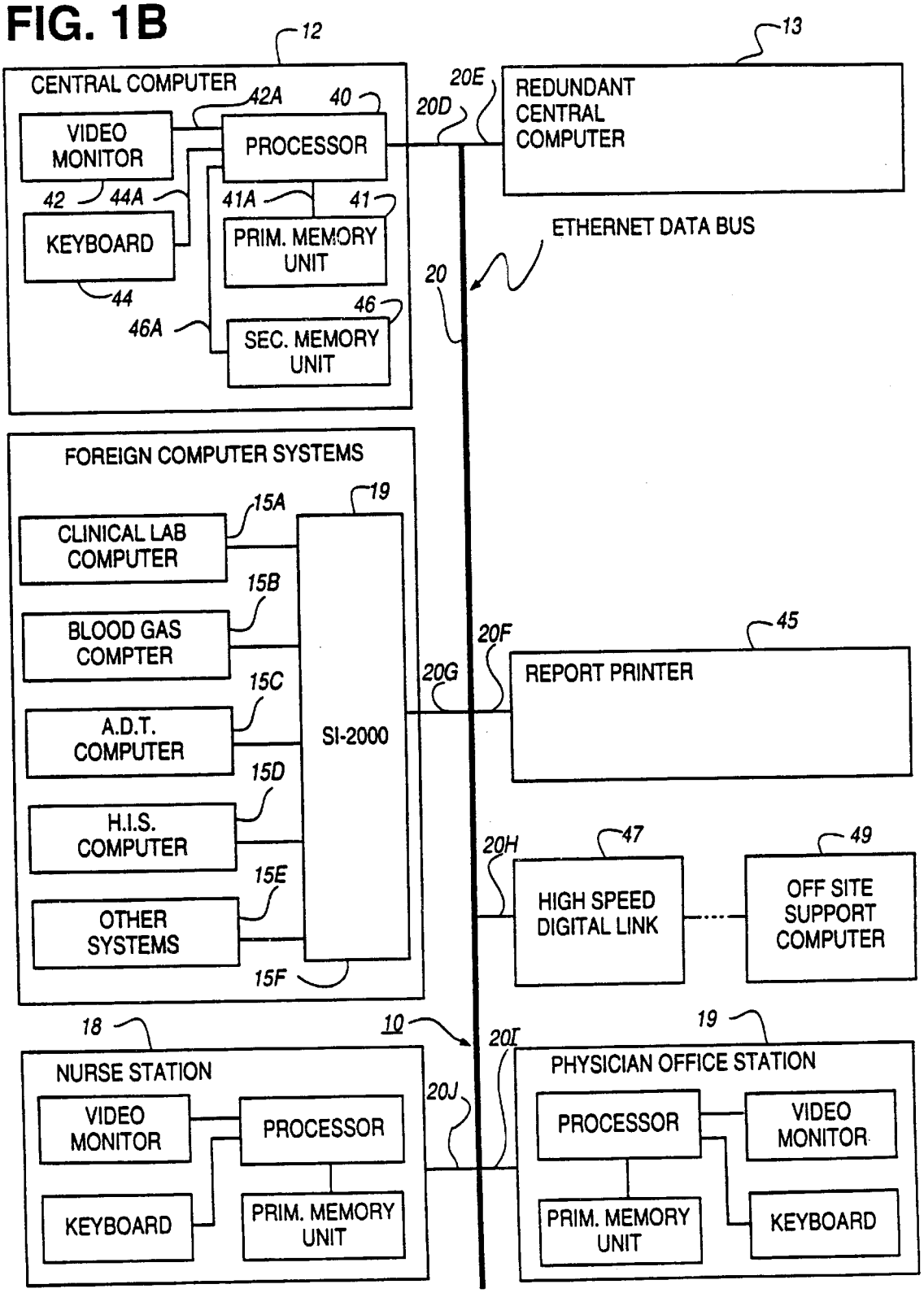

| BETHANY, FRANCINE 1490 CCU-1 1492 | PHY: TANG 1493 | ENV. 1494 | 0958 | 7 JAN 1994 1495 | 1497 |
|---|---|---|---|---|---|
| ACTIVE CARE PATHS (*) 1401 | CRITICAL CARE PATH 1496 | | | | |
| | | 7 JAN. 0935 | 8 JAN 0000 | TIME: 0935 9 JAN 0000 | 7 JAN 94 1403 |
| HIP REPLACEMENT 1430 | | OPERATIVE DAY | POST-OP DAY 1 | POST-OP DAY 2 | |
| PNEUMONIA-ATELECTASIS 1440 | | EVALUATION | EVALUATION | EVALUATION | |
| ACUITY (*) | | | | | |
| PATIENT PROBLEMS (*) | | | | | |
| SKIN INTEGRITY, IMPAIRED R/T *SURGERY AND IMMOBILITY* | 1413 | NO EVIDENCE OF SKIN BREAKDOWN 1411 -DEM- | NO EVIDENCE OF SKIN BREAKDOWN 1415 -DEM- | NO EVIDENCE OF SKIN BREAKDOWN 1417 | |
| URINARY ELIMINATION PATTERN, ALTERNATION IN: R/T *SURGERY AND IMMOBILITY* | 1414 | VOIDING PER NORMAL PATTERN 1412 -DEM- | VOIDING PER NORMAL PATTERN 1416 -DEM- | VOIDING PER NORMAL PATTERN 1418 | |
| ASSESSMENTS MEDICATIONS (*) TREATMENTS W/STANDARDS DIAGNOSTIC PROCEDURES (NONE) | | | | | 1498 |
| F1 | F2 | F3 | F4 | F5 | F6 | F7 | F8 | F9 | F10 | F11 | F12 |

FIG. 14A

CRITICAL CARE PATH

BETHANY, FRANCINE  1490  CCU-1  1492    PHY: TANG  1493    ENV.  1494  0958    TIME: 0935   7 JAN 94  1495

| ACTIVE CARE PATHS (*) | | 7 JAN. 0935 | 8 JAN 0000 | 9 JAN 0000 |
|---|---|---|---|---|
| 1 HIP REPLACEMENT 1430 | | OPERATIVE DAY EVALUATION | POST-OP DAY 1 EVALUATION | POST-OP DAY 2 EVALUATION |
| PNEUMONIA-ATELECTASIS 1440 | | | | |
| ACUITY (*) 1421 | | | | |
| FIMI GOALS  EXPECTED OUTCOMES 1425 | | | | |
| BED MOBILITY | 6 | BED MOBILITY | 6 BED MOBILITY | 4 BED MOBILITY |
| BASIC TRANSFER | 6 | BASIC TRANSFER | 6 BASIC TRANSFER | 4 BASIC TRANSFER |
| BASIC AMBULATION | 6 | BASIC AMBULATION | 6 BASIC AMBULATION | 4 BASIC AMBULATION |
| STEP AMBULATION | 6 | STEP AMBULATION | 6 STEP AMBULATION | N/T STEP AMBULATION |
| EAR AMBULATION | 6 | EAR AMBULATION | 5 EAR AMBULATION | N/T EAR AMBULATION |
| SELF CARE | 6 | SELF CARE | 6 SELF CARE | 5 SELF CARE |
|  | | 1470 -DEM- | 1471 -DEM- | 1472 -DEM- |
| URINARY ELIMINATION PATTERN, ALTERNATION IN: R/T *SURGERY AND IMMOBILITY* 1422 | | VOIDING PER NORMAL PATTERN 1412 -DEM- | VOIDING PER NORMAL PATTERN -DEM- | VOIDING PER NORMAL PATTERN 1418 -DEM- |
| ASSESSMENTS MEDICATIONS (*) TREATMENTS W/STANDARDS DIAGNOSTIC PROCEDURES (NONE) | | 1407 | 1408 | 1409 |

| F1 | F2 | F3 | F4 | F5 | F6 | F7 | F8 | F9 | F10 | F11 | F12 |
|---|---|---|---|---|---|---|---|---|---|---|---|

FIG. 14B

| BETHANY, FRANCINE | CCU-1 | PHY: TANG | ENV. | 0958 | 7 JAN 1994 |
|---|---|---|---|---|---|
| ACTIVE CARE PATHS (*) | CRITICAL CARE PATH | | | TIME: 0935 | 7 JAN 94 |
| | | 7 JAN. 0935 | 8 JAN 0000 | 9 JAN 0000 | |
| 1 | | | | | |
| HIP REPLACEMENT | | OPERATIVE DAY | POST-OP DAY 1 | POST-OP DAY 2 | |
| ACUITY (*) | | | | | |
| PATIENT PROBLEMS (*) | | | | | |
| SKIN INTEGRITY, IMPAIRED R/T *SURGERY AND IMMOBILITY* | | NO EVIDENCE OF SKIN BREAKDOWN | NO EVIDENCE OF SKIN BREAKDOWN | NO EVIDENCE OF SKIN BREAKDOWN | |
| | | -DEM- | -DEM- | | |
| URINARY ELIMINATION PATTERN, ALTERNATION IN: R/T *SURGERY AND IMMOBILITY* | | VOIDING PER NORMAL PATTERN | VOIDING PER NORMAL PATTERN | VOIDING PER NORMAL PATTERN | |
| | | -DEM- | -DEM- | | |
| ASSESSMENTS MEDICATIONS (*) TREATMENTS W/STANDARDS DIAGNOSTIC PROCEDURES (NONE) | | | | | |

| F1 | F2 | F3 | F4 | F5 | F6 | F7 | F8 | F9 | F10 | F11 | F12 |
|---|---|---|---|---|---|---|---|---|---|---|---|

FIG. 14C

```
         CARE PATH TYPE

SURGICAL DIAGNOSIS                    1486

MEDICAL DIAGNOSIS                     1485
```
                                    1453

```
  ADD CARE PATH

CARE PATH TYPE      1487
  CARE PATH NAME      1488

EVALUATION TIME  1463  START STAB.  1464

CHOICE LIST              1462
```
                                    1484

```
  ENTER CARE PATH NAME
  (DEFAULT: HIP REPLACEMENT):
```
                                    1498

```
     CONFIGURATION FILE WRITTEN
       (NEW CARE PATH NAME)

<PRESS ANY KEY TO CONTINUE>
```
                                    1499

| 1601 WINSTON, ROGER | ORTHO-4 | PHY: TANG (ENV. ORTHO) | 1039 | 19 DEC, 1994 |
|---|---|---|---|---|
| | | CRITICAL CARE PATH | | |

| ACTIVE CARE PATHS (*) | | 18 DEC 0900  1603 | 19 DEC 0900  1605 |
|---|---|---|---|
| 1602 HIP REPLACEMENT | | PRE-OP DAY 1 | OPERATIVE DAY |
| 1606 ACUITY | | | |
| PATIENT PROBLEMS (*) | | | |
| 1698 BOWEL ELIMINATION, ALTERATION IN: CONSTIPATION R/T SURGERY AND IMMOBILITY  1610 | | 1611 | 1612 |
| COMFORT, ALTERATION IN R/T MUSCLE SPASMS AND PAIN PRE & POST OP  1620 | | 1613 | PAIN CONTROLLED ON IM/PCA MEDICATIONS  1614 |
| KNOWLEDGE DEFICIT R/T SURGERY  1630 | | PATIENT VERBALIZES  1615 UNDERSTANDING OF PRE, POST AND OP PROCEDURES | PATIENT DEMONSTRATES UNDERSTANDING OF IMMEDIATE POST-OP INSTRUCTIONS  1616 |
| MOBILITY, IMPAIRED PHYSICAL R/T SURGERY, MEDICATIONS, PAIN/DISCOMFORT  1640 | | PATIENT DEMONSTRATES ABILITY TO PERFORM EXERCISES  1617 | PATIENT COMPLIES WITH BED MOBILITY  1618 |
| SPECIAL INSTRUCTIONS (*) | | | |
| TREATMENTS W/STANDARDS | | | |

| F1 | F2 | F3 | F4 | F5 | F6 | F7 | F8 | F9 | F10 | F11 | F12 |
|---|---|---|---|---|---|---|---|---|---|---|---|

FIG. 16

| WINSTON, ROGER | | | ORTHO-4 | | PHY: TANG (ENV. ORTHO) | 1039 | 21 DEC 1994 |
|---|---|---|---|---|---|---|---|
| | | | CRITICAL CARE PATH | | | TIME: 1039 | 21 DEC 94 |
| ACTIVE CARE PATHS (*) | | | 18 DEC 0900 | 19 DEC 0900 | 20 DEC 0900 | | 21 DEC 0000 |
| PNEUMONIA-ATELECTASIS | | | | | SECONDARY | | SECONDARY |
| ACUITY (*) | | | | | | | |
| PATIENT PROBLEMS (*) | | | | | | | |
| KNOWLEDGE DEFICIT R/T SURGERY | | | | | PATIENT VERBALIZES UNDERSTANDING OF PNEUMONIA/ ATELECTASIS PREVENTION | | PATIENT VERBALIZES UNDERSTANDING OF PNEUMONIA/ ATELECTASIS PREVENTION |
| SPECIAL INSTRUCTIONS (*) | | | | | | | |
| CHEST PERCUSSION/ POSTURAL DRAINAGE | | | | | | | |
| TREATMENTS | | | | | | | |
| F1 | F2 | F3 | F4 | F5 | F6 | F7 | F8 | F9 | F10 | F11 | F12 |

FIG. 17

| WINSTON, ROGER | ORTHO-4 | PHY: TANG (ENV. ORTHO) | 1039 | 21 DEC 1994 |
|---|---|---|---|---|
| ACTIVE CARE PATHS (*) | CRITICAL CARE PATH | | TIME: 1039 | 21 DEC 94 |
| | 18 DEC 0900 | 19 DEC 0900 | 20 DEC 0000 | 21 DEC 0010 |
| HIP REPLACEMENT | PRE-OP DAY 1 | OPERATIVE DAY | PRE-OP DAY 1 | PRE-OP DAY 2 |
| PNEUMONIA-ATELECTASIS | | | SECONDARY | SECONDARY |

| ACUITY (*) PATIENT PROBLEMS (*) | | | | |
|---|---|---|---|---|
| BOWEL ELIMINATION ALTERATION IN: CONSTIPATION R/T SURGERY AND IMMOBILITY | | | | |
| COMFORT, ALTERATION IN R/T MUSCLE SPASMS AND PAIN PRE & POST OP | | PAIN CONTROLLED ON IM/PCA MEDICATIONS | -DEM- | -DEM- |
| KNOWLEDGE DEFICIT R/T SURGERY | PATIENT VERBALIZES UNDERSTANDING OF POST AND OP PROCEDURES | PATIENT DEMONSTRATES UNDERSTANDING OF IMMEDIATE POST-OP INSTRUCTIONS | PATIENT VERBALIZES UNDERSTANDING OF PRE, POST AND OP PORCEDURES -DEM- | PATIENT VERBALIZES UNDERSTANDING OF PRE, POST AND OP PORCEDURES -DEM- |
| KNOWLEDGE DEFICIT R/T MEASURES TO PREVENT REOCCURRENCE | | | PATIENT VERBALIZES UNDERSTANDING OF PNEUMONIA/ ATELECLASS PREVENTION | PATIENT VERBALIZES UNDERSTANDING OF PNEUMONIA/ ATELECLASS PREVENTION |
| MOBILITY, IMPAIRED PHYSICAL R/T SURGERY, MEDICATIONS, PAIN/DISCOMFORT | PATIENT DEMONSTRATES ABILITY TO PERFORM EXERCISES | PATIENT COMPLIES WITH BED MOBILITY | PATIENT DEMONSTRATES ABILITY TO PERFORM EXERCISES -DEM- | PATIENT DEMONSTRATES ABILITY TO PERFORM EXERCISES -DEM- |

| SPECIAL INSTRUCTIONS (*) | | | | |
|---|---|---|---|---|
| CHEST PERCUSSION/POSTURAL DRAINAGE | | | | |
| TREATMENTS W/STANDARDS | | | | |

| F1 | F2 | F3 | F4 | F5 | F6 | F7 | F8 | F9 | F10 | F11 | F12 |

FIG. 18

| WINSTON, ROGER | ORTHO-4 | PHY: TANG (ENV. ORTHO) | | 21 DEC 1994 |
|---|---|---|---|---|

CRITICAL CARE PATH

EDIT LABELS

NAME        KNOWLEDGE DEFICIT

COMMENT   R/T - MEASURE TO PREVENT RECURRENCE

START TIME  0938 20 DEC 1994         D/C TIME

<TAB>          NEXT FIELD
<SHIFT TAB>   PREVIOUS FIELD

| | | | | | |
|---|---|---|---|---|---|
| 0  | - R/T - | BREASTFEEDING | 15 | - R/T - | MEDICATION REGIMEN |
| 1  | - R/T - | CHILDBIRTH | 16 | - R/T - | METHODS OF ALLEVIATING/ REDUCING SIDE EFFECTS |
| 2  | - R/T - | CHILD CARE | | | |
| 3  | - R/T - | CULTURAL BARRIER | 17 | - R/T - | NORMAL GROWTH AND DEVELOPMENT |
| 4  | - R/T - | DETECTION AND PREVENTION OF COMPLICATIONS | | | |
| | | | 18 | - R/T - | POSSIBLE LIFESTYLE MODIFICATIONS |
| 5  | - R/T - | DIAGNOSIS | 19 | - R/T - | PROCEDURE |
| 6  | - R/T - | DIET | 20 | - R/T - | REHABILITATIVE THERAPIES |
| 7  | - R/T - | DISEASE/CONDITION AND NEED FOR LIFELONG TREATMENT | 21 | - R/T - | SELF-CARE |
| | | | 22 | - R/T - | STRESS REDUCTION |
| 8  | - R/T - | DISEASE PROCESS | 23 | - R/T - | TREATMENT PLAN |
| 9  | - R/T - | ENVIRONMENTAL HAZARDS | 24 | - R/T - | UNFAMILIAR WITH COMMUNITY RESOURCES |
| 10 | - R/T - | EXERCISE | | | |
| 11 | - R/T - | FAMILY PLANNING | 25 | - R/T - | WOUND CARE |
| 12 | - R/T - | FOLLOW UP CARE | | | |
| 13 | - R/T - | HOME CARE | | | |
| 14 | - R/T - | MEASURES TO PREVENT RECURRENCE | | | |

| F1 | F2 | F3 | F4 | F5 | F6 | F7 | F8 | F9 | F10 | F11 | F12 |
|---|---|---|---|---|---|---|---|---|---|---|---|

| WINSTON, ROGER | ORTHO-4 | PHY: TANG (ENV. ORTHO) | 1039 | 21 DEC 1994 |
|---|---|---|---|---|

CRITICAL CARE PATH

| ACTIVE CARE PATHS (*) | | | TIME: 1039 | 21 DEC 94 |
|---|---|---|---|---|
| | 18 DEC 0900 | 19 DEC 0900 | 20 DEC 0000 | 21 DEC 0010 |
| 2301 — HIP REPLACEMENT | PRE-OP DAY 1 | OPERATIVE DAY | POST-OP DAY 1 | POST-OP DAY 2 |
| ACUITY (*) | | | | |
| PATIENT PROBLEMS (*) | | | | |
| ASSESSMENTS | | | | |
| 2310 — CARDIOVASCULAR | | | | |
| 2311 — NEUROLOGICAL | | | | |
| 2312 — RESPIRATORY | | | | |
| 2313 — GASTROINTESTINAL | | | | |
| 2314 — GENITOURINARY | | | | |
| 2315 — INTEGUMENTARY | | | | |
| 2316 — MUSCULOSKELETAL | | | | |
| 2317 — NEUROVASCULAR | | | | |
| 2318 — INCISIONAL/DRESSING | | | | |
| 2319 — PSYCH/SOCIAL | | | | |
| 2320 — PAIN | | | | |
| ACTIVITY | | | | |

| F1 | F2 | F3 | F4 | F5 | F6 | F7 | F8 | F9 | F10 | F11 | F12 |
|---|---|---|---|---|---|---|---|---|---|---|---|

2300

| WINSTON, ROGER | ORTHO-4 | PHY: TANG (ENV. ORTHO) | | 21 DEC 1994 |
|---|---|---|---|---|
| ACTIVE CARE PATHS (*) | | | TIME: 1039 | 21 DEC 94 |
| | 18 DEC 0900 | 19 DEC 0900 | 20 DEC 0000 | 21 DEC 0010 |
| PNEUMONIA-ATELECTASIS | | | SECONDARY | SECONDARY |
| ACUITY (*) | | | | |
| PATIENT PROBLEMS (*) | | | | |
| ASSESSMENTS | | | | |
| CARDIOVASCULAR | | | | |
| NEUROLOGICAL | | | | |
| RESPIRATORY | | | | |
| GASTROINTESTINAL | | | | |
| MUSCULOSKELETAL | | | | |
| NEUROVASCULAR | | | | |
| PSYCH/SOCIAL | | | | |
| PAIN | | | | |
| ACTIVITY | | | | |

CRITICAL CARE PATH

2400

2403 — PNEUMONIA-ATELECTASIS

2410 CARDIOVASCULAR
2411 NEUROLOGICAL
2412 RESPIRATORY
2413 GASTROINTESTINAL
2414 MUSCULOSKELETAL
2415 NEUROVASCULAR
2416 PSYCH/SOCIAL
2417 PAIN

| F1 | F2 | F3 | F4 | F5 | F6 | F7 | F8 | F9 | F10 | F11 | F12 |

FIG. 24

| WINSTON, ROGER | | ORTHO-4 | PHY: TANG (ENV. ORTHO) | | | 21 DEC 1994 |
|---|---|---|---|---|---|---|
| | | | CRITICAL CARE PATH | | TIME: 1039 | 21 DEC 94 |
| ACTIVE CARE PATHS (*) | | 18 DEC 0900 | 19 DEC 0900 | 20 DEC 0000 | 21 DEC 0010 | |
| 2501 — HIP REPLACEMENT | | PRE-OP DAY 1 | OPERATIVE DAY | POST-OP DAY 1 | POST-OP DAY 2 | |
| 2503 — PNEUMONIA-ATELECTASIS | | | | SECONDARY | SECONDARY | |
| ACUITY (*) | | | | | | |
| PATIENT PROBLEMS (*) | | | | | | |
| ASSESSMENTS | | | | | | |
| 2510 — CARDIOVASCULAR | | | | | | |
| 2511 — NEUROLOGICAL | | | | | | |
| 2512 — RESPIRATORY | | | | | | |
| 2513 — GASTROINTESTINAL | | | | | | |
| 2514 — GENITOURINARY | | | | | | |
| 2515 — INTEGUMENTARY | | | | | | |
| 2516 — MUSCULOSKELETAL | | | | | | |
| 2517 — NEUROVASCULAR | | | | | | |
| 2518 — INCISIONAL/DRESSING | | | | | | |
| 2519 — PSYCH/SOCIAL | | | | | | |
| 2520 — PAIN | | | | | | |
| ACTIVITY | | | | | | |

| F1 | F2 | F3 | F4 | F5 | F6 | F7 | F8 | F9 | F10 | F11 | F12 |
|---|---|---|---|---|---|---|---|---|---|---|---|

FIG. 25

CLINICAL CRITICAL CARE PATH SYSTEM AND METHOD OF USING SAME

This application a continuation of application Ser. No. 08/396,004, filed Feb. 28, 1995, (now abandoned).

TECHNICAL FIELD

The present invention relates in general to a clinical information system and a method for using it for patient charting or record keeping purposes. The invention more particularly relates to a clinical critical care path system, which facilitates the ability for an improved careful maintenance of patient care.

BACKGROUND ART

Charting the progress of a patient after being admitted to a medical care facility for medical or surgical reasons has been a traditional practice in the medical profession. Such charting typically involves monitoring the condition of a patient, collecting information relative to the physical condition of the patient, and logging the collected information onto a patient chart for review and analysis by trained medical personnel.

To make such charting more efficient and cost effective, various monitoring and information gathering systems have been developed to provide automatic clinical record management. For example, reference may be made to the following United States patents and published articles, as follows: U.S. Pat. Nos. 5,361,202; 5,267,155; 5,077,666; 5,072,383; 4,893,270; 4,878,175; 4,838,275; 4,815,474; 4,803,625; 4,731,726; 4,712,562; 4,695,954; 4,674,652; 4,665,499; 4,622,185; 4,577,638; 4,531,527; 4,519,398; 4,513,294; 4,489,387; 4,473,884; 4,465,077; 4,428,381; 4,422,081; 4,417,306; 4,412,292; 4,363,368; 4,347,213; 4,320,766; 4,296,756; 4,272,878; 4,270,547; 4,227,526; 4,216,462; 4,197,854; 4,173,971; 4,151,831; 4,150,284; 4,130,881; 4,004,577; 3,996,928; 3,963,019; 3,910,257; 3,872,448; 3,872,251; 3,830,896; 3,765,406; 3,726,270; 3,696,805; 3,426,150; 3,302,828; 3,106,701; 2,891,111; and 1,078,090; and Walter A. Shewhart, Ph.D., *Statistical Method from the Viewpoint of Quality Control*, © 1939; pp. 1–49; Donald Del Mar, George Sheldon, *Introduction to Quality Control*, © 1988, pp. 123–143; Irvin W. Burr, *Statistical Quality Control Methods*, © 1976, pp. 23–35; *Indirect Heart Rate Measuring Device*, Wilberger, 1994; American J. of Medical Elec., *Light Wt. Carbon Fiber Structures . . .* , Manley et al., 1973; Composites, Data Communications, November 1986, Principi et al., *William Beaumont Hospital and Its Generation System*, U.S. Healthcare, Vol. 6, No. 3, March 1998, Childs; *Evaluating Automated Information Systems*, Mowra et al., Vol.5, No. 1, January/February 1987, Nursing Economics: *Automated Information Systems in Quality Assurance*, Mowra et al., Nursing Economics, September/October 1987; *Doctor Office Manager: An IBM Billing Package*, Abstract of Article Appearing in M.D. Computing Vol. 2, No. 3, pp. 23–30, 6/85, Abstract from Microsearch File of Orbit AN85-026189; J. E. Brimm, *Computers in Critical Care*, March 1987, pp. 53–63, Critical Care Nursing Quarterly, Hewlett Packard, 78707A; *PDMS Clinical User's Guide*, January 1982, pp. 1-1 through 1-34, 10-1 through 10-5, 15-1 through 15-2; Hewlett Packard; *PDMS System Description*, 1982, pp. 1-1 through 2-23; Health Data Science Corp. Ulticare (presumably 10/84), pp. 1–9; Ralph A. Korpman, *Patient Care Information Systems—Looking to the Future*, Software in Healthcare, Parts 1–5, April/May 1984–December/January 1984–1985; *An Integrated Bedside Fetal Monitor and Obstetrical Data System*, IEEE Eng. In. Med. & Biology Med., September 1984, pp. 22–24; and *U.S. Healthcare*, Vol. 6, No. 3, March 1989, each of the foregoing patents and published articles being incorporated herein by reference as though fully set forth herein.

As disclosed in the foregoing publications, various clinical information systems display, monitor and chart patient physiological conditions. Such systems enable a user to enter information regarding the condition of a patient and to have lists of tasks to be performed regarding a patient to be generated.

While such systems may have been satisfactory for some applications, they have not proven to be entirely satisfactory for some applications relative to improving patient management on a cost effective basis. More particularly, a treatment plan for each new patient would still necessitate suitable preparation, usually by more than one highly trained healthcare provider. Such preparation time, while an important task, has been burdensome and not always efficient and cost effective.

With the rapid rise in medical treatment costs and hospitalization costs, it has become very important to be more efficient to achieve overall cost saving reductions. To achieve such cost savings, delivery of care to large groups of patients must be consistent. In this regard, consistent delivery of care requires detailed documentation for each patient and periodic monitoring of each patient to evaluate patient progress.

Consistent delivery therefore requires a definitive plan to enable healthcare providers to provide high quality care. Such a plan optimizes delivery of care, results in quicker patient recovery, helps to eliminate unwanted and undesired interventions. In short, such a plan is designed to achieve the desired goals for a patient.

Thus, for any given medical condition, to achieve cost saving reductions there must be uniform and consistent delivery of healthcare; measurable objective documentation; and detailed standard of care procedures.

One attempt at achieving the consistent standard of care and the provision of detailed documentation by the healthcare providers has been to develop a pre-printed critical care path document or form which incorporates predefined hospital standard of care procedures, care provider orders and expected outcome results for a given diagnosis.

While such critical care flow forms may have helped to improve patient management and improved system utilization to a certain degree, such critical care flow sheets have not proven entirely satisfactory. In this regard, the typical preprinted critical care path document for any given diagnosis is a document which is very difficult to use and to read. It contains a large number of small-sized time-line spaces for entry of the patient deviation codes for each day of treatment, or for each stage of patient care. Such small spaces result in small handwritten entries which can be illegible, or which can lead to an unwanted and undesirable transcription error of some type.

The entry of only code information requires utilizing another form for entry of the deviation information. The description of the deviation or other desired information as an explanation of the simple code information entered on the care path sheet, must be entered on other sheets of paper. Thus, not only unwanted and undesirable transcription errors can result, but also all necessary patient information is not available on a single document. Instead, multiple forms must be employed for entry of code information and text information.

Still yet another problem associated with preprinted critical care path flow sheets is that the preprinted critical care path flow sheets are configured for a single diagnosis activity only, such as a treatment plan for a patient undergoing hip replacement surgery. In this regard, if a patient is confined to a treatment facility and requires treatment for two or more surgical activities, or if a secondary diagnosis arises, such as where a surgical patient subsequently develops a medical problem, such single critical care path forms cannot be used. The preprinted forms do not have sufficient space to permit the addition of other care paths for multiple diagnoses. Moreover, if two or more single diagnosis forms are used, conflicting treatment plans may result. More particularly, pre-printed forms are not necessarily detailed enough for a given patient. For example, a patient involved in an automobile accident nay have a broken arm, require surgery to stop internal bleeding, be a diagnosed diabetic, require a hip replacement and develop secondary pneumonia two days after admission for treatment. Each diagnosed problem, in turn, could result in a multiple number of deviations. In short, because of the large number of permutations and combinations the use of multiple flowsheet documents greatly decreases efficiency.

Therefore, it would be highly desirable to have a new and improved clinical information system which can facilitate greatly the development and execution of a patient care plan, even where there exists multiple clinical diagnoses whether medical, surgical or a combination thereof.

DISCLOSURE OF INVENTION

Therefore, the principal object of the present invention is to provide a new and improved method and apparatus for facilitating the implementation and execution of clinical critical care path information for patients.

Another object of the present system is to provide such a new and improved method and apparatus which can assist healthcare providers in implementing and executing such plans where multiple diagnoses exist or occur subsequent to the commencement for a treatment plan for a single diagnosis.

Briefly, the above and further objects of the present invention are realized by providing a new and improved clinical critical care path system, which can be tailored readily for a given patient diagnosis for either single or combined medical and/or surgical diagnoses.

The clinical information system stores critical care information for various patient diagnoses and retrieves them for a given patient. Treatment information is tailored to a given patient by enabling selected treatment information to be edited. Where multiple diagnoses are present, the prescribed or ordered treatment plans for each diagnosis are merged for a given patient, and potential conflicts are determined for any ordered activity. Upon determination of a conflict, patient treatment information is repeated on separate display lines to alert the healthcare provider to permit the healthcare provider to analyze the conflict and to determine what order or orders should be entered. Customized multiple diagnosis treatment information can then be entered and stored for a given patient.

BRIEF DESCRIPTION OF DRAWINGS

The above mentioned and other objects and features of this invention and the manner of attaining them will become apparent, and the invention itself will be best understood by reference to the following description of the embodiment of the invention in conjunction with the accompanying drawings, wherein:

FIGS. 1A and 1B, when arranged as indicated in FIG. 1, is a block diagram of a clinical critical care path information system which is constructed in accordance with the present invention;

FIGS. 14A–C illustrate a critical care path screens;

FIG. 16 illustrates a critical care path screen generated by the system of FIG. 1 illustrating a single medical diagnosis active care path;

FIG. 17 illustrates a critical care path screen generated by the system of FIG. 1, illustrating a single surgical diagnosis active care path;

FIG. 18 illustrates a critical care path screen generated by the system of FIG. 1, illustrating a merged pair of active care paths;

FIG. 19 illustrates an edit cell window of a critical care path screen produced by the system of FIG. 1;

FIG. 23 illustrates a critical care path screen generated by the system of FIG. 1 illustrating a single medical diagnosis active care path;

FIG. 24 illustrates a critical care path screen generated by the system of FIG. 1, illustrating a single surgical diagnosis active care path; and FIG. 25 illustrates a critical care path screen generated by the system of FIG. 1, illustrating a merged pair of active care paths.

BEST MODE FOR CARRYING OUT THE INVENTION

Figures 2, 3:
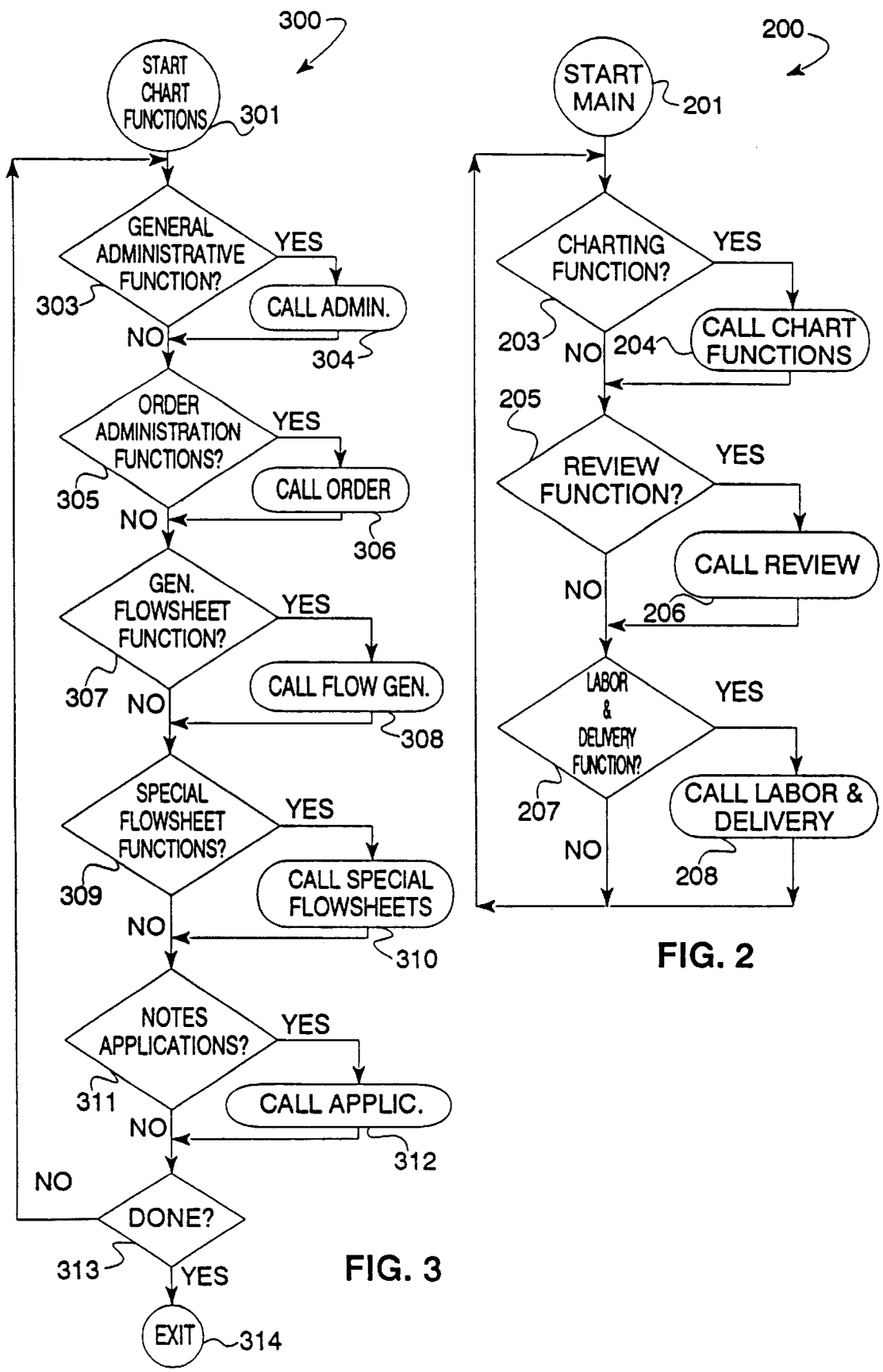
FIGS. 2–13 are simplified flowchart diagrams of the computer program executed by the computer of the system of FIG. 1.

The following description is presented and organized according to the following outline:
A. SYSTEM HARDWARE DESCRIPTION
B. SYSTEM OPERATION
C. SYSTEM COMPUTER SOFTWARE
  1. ADD ACTIVE CARE PATH
  2. ADD NEW ROW
  3. MODIFY ROW
  4. DISCONTINUE ROW

A. System Hardware Description

Referring now to FIG. 1 of the drawings, there is shown a computerized critical care path system 10, which is constructed in accordance with the present invention and which is adapted to generate automatically critical care flowsheet information for multiple treatment diagnoses, whether medical, surgical or a combination thereof. The system 10 further assists healthcare providers in modifying such flowsheet information on the occurrence of certain exceptions or conflicts between standard predefined standard of care treatment plans. In short, the critical care path system 10 can perform many functions including integrating or merging flowsheet information for separate and distinct medical and surgical diagnoses and customizing or tailoring flowsheet information. In this regard, the system 10 enables a user to tailor the critical care path parameters to customize the critical care path for any given patient.

In short, the system 10 facilitates the monitoring of the standard of care of a large number of patients who are confined at various patient bedside locations, such as a patient 15 located at a bedside location 14. Such a system optimizes delivery of care to patients, enables quicker patient recovery, eliminates undesired and unwanted interventions and achieves a more consistent form of care for each patient in a highly efficient manner. Thus, cost saving are realized for the healthcare provider and desired results are achieved for the patients.

Although the phrase "critical care path" has been employed to describe the present invention, it should be understood that other similar phrases can be used. Such phrases include, but are not limited to: "critical path," "care path," and "care map."

The system 10 generally includes a group of patient bedside monitoring locations located through the facility of a healthcare provider. Such locations would be in an emergency room, an intensive care unit, a cardiac unit, and so forth.

Each patient bedside location, such as the location 14 includes a bedside display station and a group of bedside data acquisition devices, such as bedside display station 16 and group 17 of bedside data acquisition devices. The display station allows healthcare providers to observe the patient while entering deviation information at bedside while the data acquisition devices facilitate the gathering of patient data and enable healthcare providers to monitor the condition of a patient at bedside.

In order to facilitate central monitoring, the system 10 also includes a central computer 12 (FIG. 1B) which communicates individually and selectively with the bedside display stations, such as the display station 16.

As will be explained hereinafter in greater detail, the central computer 12 and its associated software gathers and stores patient information, creates flowsheet information, establishes critical care path information for facilitating patient care and to manage the flowsheet information being compiled. The system 10 enables each bedside displays station as well as other healthcare provider computer arrangements such as a nurse station computer 18, and a physician station computer 19 to access such information so healthcare providers can optimize delivery of care to patients.

The central computer 12 and each bedside patient location display station are coupled together via a data bus, such as an ethernet clinical data bus 20. For example, the central computer 12 is coupled to the data bus 20 via a lead or cable 20D, while the bedside display station 16 is coupled to the bus 20 via a lead or cable 20C. In this manner, a healthcare provider/user can monitor and enter patient information from many different locations.

In order to provide a more fail-safe and secure operation, the system 10 also includes a redundant central computer 13. An off-site support computer 49 is coupled to the data bus 20 via a high speed data link 47 to provide information to remote locations. A report printer 45 is coupled to the data bus 20 via a lead or cable 20F to enable system users to obtain hard copy reports, flowsheets and other documents for providing efficient patient care.

As best seen in FIG. 1B, the redundant computer 13, the nurse station 18, the physician station 19 and the high speed digital link 47 are coupled to the data bus 20 via leads or cables 20E, 20J, 20I and 20H, respectively.

As best seen in FIG. 1A, the group 17 of bedside data acquisition devices includes a ventilator 27, a gas monitor 28, an IV pump 29, a fetal monitor 30, other monitoring devices, such as a special bedside device 31 and a physiologic monitor 32. The devices 27–31 and 32 are coupled to the data bus 20 via a DAS interface 33 having a lead or cable 20B, and monitor network interface 34 having a lead or cable 20A, respectively.

The system 10 via the central computer 12 is coupled to each group of bedside acquisition devices, such as the group 17 of bedside data acquisition devices for the purpose of monitoring each patient in the healthcare provider facility. In this regard, the central computer 12 gathers information from the data acquisition devices, receives information from various healthcare providers regarding patient diagnoses and, in turn, generates customized critical care path information for each patient.

The customized critical care path information is, in turn, utilized by the control computer 12 to manage the compiling of flowsheet information for each patient. The flowsheet information is an ongoing compilation of patient information for each patient.

For example, with respect to the group 17 of bedside data acquisition devices, those skilled in the art will understand that as each patient requires customized care, certain ones of the monitoring devices may not be required. Also, which interface device or devices are required, such as the devices 33 and 34, depends on the type of data acquisition devices utilized for monitoring a patient, such as the patient 15. Thus, in accordance with the customized care path information, the system 10 determines that certain rows of the flowsheet maybe unnecessary to cause them to be unused whenever it is determined that a certain bedside data acquisition device is not required for a certain patient. In short then, the critical care path information is used by the central computer 12 to manage the flowsheet information causing it to be appropriately compiled for each particular patient being monitored by the system 10. In this manner, a more consistent form of care for each patient is facilitated in a highly efficient process.

Considering now the central computer 12 in greater detail with reference to FIG. 1B, the central computer 12, includes a processor 40 having coupled thereto a primary 25 memory unit 41, such as a random access memory unit, a monitor 42, a keyboard 44 and a secondary memory unit 46, such as a disc drive memory unit. The central computer 12 is generally a super mini-computer, such as sold by Digital Equipment Corporation, Inc. and others. The computer processor 40 is interconnected to the memory unit 41 via a memory cable 41A, the monitor 42 via a video cable 42A, the keyboard 44 via a keyboard cable 44A, and the secondary memory unit 46 via a memory post cable 46A. The primary memory unit 41 and the secondary memory unit 46 contain the long term database information for the critical care path system, and the application software to receive patient data from the bedside display station 16.

The processor 40 and its associated application software performs all the necessary functions of critical care path patient maintenance including 1) retaining clinical information for retrieval and review; 2) performing requested clinical calculations; 3) displaying patient data in tabular and graphic formats; 4) allowing simultaneous multiple user access to any given patient chart information; and 5) intergrating patient data acquired from the bedside data acquisition terminals and other acquisition systems such as a clinical laboratory information computer system 15A, a blood gas laboratory computer information system 15B, an A.D.T. (admissions discharges and transfers) computer information system 15C, an H.I.S. (hospital information system) information system 15D, and other foreign systems, such as a foreign computer system 15E.

As best seen in FIG. 1B, an interface unit, such as an SI2000 interface unit 15F, enables such other systems 15A–15E to be coupled to the data bus 20 shared by the central computer 12, the redundant computer 13, and the off-site support computer 49.

Considering now the bedside display station 16 in greater detail with reference to FIG. 1A, the bedside station 16 includes a central processor 22, keyboard 24, video monitor 25 and a primary memory unit 26 such as a random access memory unit. The display station 16 is disposed at the patient bedside location 14 so the healthcare provider can be in close contact with the patient as information regarding the condition of the patient is entered into the system 10.

The redundant central computer 13 is substantially similar to the central computer 12, and will not be described in greater detail. Those skilled in the art, however, will understand that all of the functions performed by the central computer 12 can also be performed by the redundant computer 13, as well as any other computer system coupled to the data bus 20 having sufficient speed and secondary memory capability. In this regard, the system 10 has a redundant capability.

B. System Operation

As noted earlier, the critical care path system 10 is a hardware and software system that automates clinical charting and completely eliminates handwritten charting. In this regard, the system 10 operates under a master or main program 200 (FIG. 2) that starts whenever the central computer 12 is activated. In this regard, the system 10 is adapted to be active or ON at all times, since critical care path patient maintenance typically requires twenty-four hour per day, seven day per week monitoring. As all of the system stations can operate independently and simultaneously using the same application software, only the operation of the central computer 12 will be discussed. For clarity purposes in understanding the operation of the system, reference may be made from time to time to other stations or data acquisition units.

In operation, and by way of example consider a patient is admitted to a healthcare facility for a surgical hip replacement procedure. A designated healthcare provider user utilizing the system 10 via the physician station, 19 enters the patients name, the surgical diagnosis and any special orders. The entered information is transferred via the lead or cable 20I to the data bus 20 and thence lead or cable 20D to the central computer 12.

The central computer 12 via the processor 40 causes the information to be processed and stored in the secondary memory unit 46 via the memory port lead 46A. In this regard, the central computer 12 retrieves selectively under user control, critical care path information. The user, in turn, can merge critical care path information for multiple diagnoses or customize the critical care path information for the patient. In this regard, certain critical care path information may be modified for the needs of the specific patient. For example, some information may not be applicable to the patient. The user may also at this time identify which group of bedside data acquisition monitors, such as group 17, that will be utilized for both pre and post operation data acquisition purposes.

After the healthcare provider/user has tailored the critical care path information, the user can cause the information to be stored in the secondary memory unit 46, for subsequent access by support personnel at the bedside of the patient via a display station, such as the display station 16. Such information may also be accessed by the nurse station 18 and the physician office station 19.

When the central computer 12 receives the tailored or customized critical care path information, the central computer 12 causes customized flowsheet information to be compiled based upon the critical cart path information. In this regard, flowsheet information is initially stored in a universal format for displaying many possible patient management information received from the display station 16 and the group 17 of bedside data acquisition devices. However, based on the customized critical care path information, certain monitors and/or devices may or may not be required for a given patient. Thus, the central computer 12 will cause the flowsheet rows for such non-used devices to be unused in the universal format resulting in a customized flowsheet for the specific patient.

After the patient is at bedside, patient information is gathered by the healthcare provider/user via the display station 16, and the appropriate bedside devices and then stored in the central computer secondary memory unit 46 for subsequent retrieval and display. In this regard, the ethernet data bus 20 has common access to each of the systems, computers, and devices via the leads or cables 20A–D and G.

More particularly, a healthcare provider user at any time thereafter, can access the stored critical care path information, the flowsheet information, and other relevant patient information stored at the central computer 12 via the bedside display station 16, the nurse station 18, and the physician office station 19.

From the foregoing, it should be understood that the system 10 facilitates the management of the care of a large group of patients. The management of care is accomplished by creating and storing in the secondary memory unit 46 of central computer 12, critical care information for a large number of different patient diagnoses, both medical and surgical. More particularly, the critical care information is indicative of expected outcomes resulting from predefined standards of care treatment plans to be administered selectively to patients.

The central computer 12 and its associated hardware and software, under user control, modifies the critical care path information for a given patient. The critical care information is then utilized to modify generalized flowsheet information to establish customized flowsheet information for each patient. Thus, certain rows of flowsheet information may not be used for given patients.

In FIG. 2, a flowchart is shown, illustrating the steps taken by the computer processor 40 in automating clinical charting functions, in reviewing database information and in monitoring patient care functions, such as labor and delivery functions. Starting in a START instruction 201, the flowchart program proceeds to a decision instruction 203 which determines whether a system user requires the system to perform any charting functions. The charting functions performed by the system 10 include:

1 General Administrative Functions
   a. Patient Admission Functions
   b. Patient Discharge Functions
2. Order Administration Functions
   a. Order Entry Review
   b. Order Entry Function
3. General Flowsheet Functions
   a. Flow Sheet Review
   b. Basic Functions
4. Special Flowsheet Functions
   a. Vital Sign Functions
   b. Intake and Output Function
   c. Medication Administration Functions
   d. Critical Care Path Functions
   e. Care Path Assessment Functions
   f. Integrated Chart Functions
5. Note Application
   a. Notes Applications Functions
   b. Care Plan Functions The flowsheets created as a result of the flowsheet functions manage patient information. The flowsheet information, in turn, is controlled by the critical care path information tailored for a particular patient by the healthcare provider user.

If the system user requires a charting function to be performed, the program advances to a call instruction 204 which causes a CHARTING subroutine 300 (FIG. 3) to be executed. After the CHARTING subroutine 300 has been executed, the program advances to a decision instruction 205. The CHARTING subroutine 300 will be described hereinafter in greater detail.

If the system user does not require the system to perform any charting functions, the program next determines in the decision instruction 205 whether the system user requires the system to perform any review functions. The review functions performed by the system 10 include:

1. Data Presentation Functions
   a. Reviewing the Information Presentation Screen
   b. 24 Hour Summary Functions
2. Special Review Screens
   a. Cardiac Output Functions
   b. Trend Plot Functions
3. Waveforms
   a. Waveform Screen Functions
4. Cardio-Respirogram Functions
   a. Cardio-Respirogram Screen Functions
5. Reference Library Functions
   a. New Reference Library Screen Functions If a review function is requested by the system user, the program proceeds to a call instruction 206 which causes a REVIEW subroutine to be executed.

If the user is not requesting to use a review function, the program goes from the decision instruction 205 to a decision instruction 207 which determines whether the user desires to use the system 10 to monitor a patient care function.

If the user desires to monitor a patient, the program proceeds to a call instruction 208 which causes a LABOR AND DELIVERY subroutine to be executed. The LABOR AND DELIVERY subroutine facilitates maternal and fetal charting functions to be selected, reviewed, changed and customized.

After the REVIEW subroutine is executed, the program returns to the decision instruction 207 and proceeds as described previously.

If at decision instruction 207 it is determined the user does not desire to use the system to monitor a patient care function, the program proceeds directly to the decision instruction 203 and continues as described previously.

Considering now the critical care path technique, the critical care path system 10 generally performs many functions including integrating or merging critical care path information for separate and distinct medical and surgical diagnoses and customizing or tailoring the care path information as will be described in greater detail under the charting functions subroutine 300.

Considering now the operation of the system in still greater detail, whenever a patient is admitted to a hospital for medical or surgical treatment, a team of healthcare providers confer to determine what treatments, medications, therapies, and other procedures, if any, should be administered to the patient to achieve expected results. In this regard, primary care facilities have developed "Standard of Care" procedures, which must be followed by those healthcare providers operating within the primary care facility. Such Standard of Care outlines and procedures define pre-configured standard orders that a patient is to receive when he or she is admitted to the facility for any diagnosed condition.

Utilizing a database of such pre-configured standard orders, the system 10 generates flowsheets for medications, intake fluids, IV drugs, TPN, output fluids, treatments, and other task oriented items. Thus, whenever a patient is introduced into the system 10 with a diagnosed medical or surgical condition, the pre-configured standard orders are routinely entered and then reviewed and analyzed by certain ones of the primary care personnel. The system 10 then transfers the orders to a critical care path and its applicable flowsheets for charting purposes. Individual orders may also be customized, entered and transferred to applicable flowsheets whenever a patient has multiple diagnosed conditions and/or does not respond to treatments as expected.

In order to facilitate a user friendly environment for automating clinical charting, the system 10 generates a series of screens and reports which are arranged to best emulate conventional hospital paper flowsheets (not shown). In this regard, the arrangement of system rows, choice lists, displayed parameters, section and reports is referred to as a hospital configuration.

As best seen in FIG. 14A, each critical care path screen generated by the system 10 is arranged into four parts that includes: a demographic bar 1490 at the top of each screen which includes the name of the patient 1491, the unit and bed number assigned to the patient 1492, the name of the primary care physician 1493, the environment 1494, and the current time and date 1495. A title bar 1496 disposed below the demographic bar 1490 contains the title of the selected screen. Next, and directly below the title bar 1496 is an application section indicated generally at 1497 that contains textual and graphic information relative to the selected screen function. At the bottom of the screen appears a soft function key label template 1498 that will be described hereinafter in greater detail.

Figure 20:
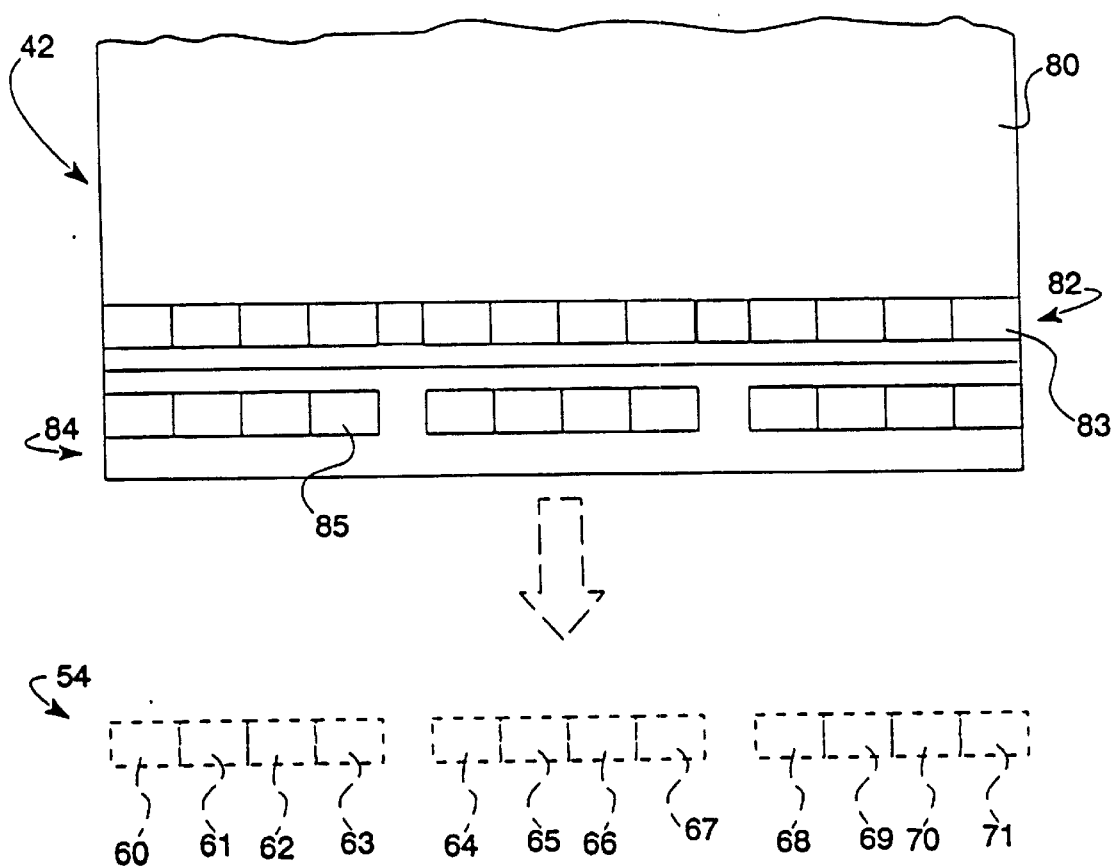
FIG. 20 is a diagrammatic view of a keyboard of FIG. 1.

Referring now to FIG. 20 there is illustrated the keyboard 44. The keyboard 44 includes an eighteen key numeric pad 50, an alphanumeric QWERTY type keyboard 52, and a function key group 54 having twelve application function keys 60–71.

Figure 21:
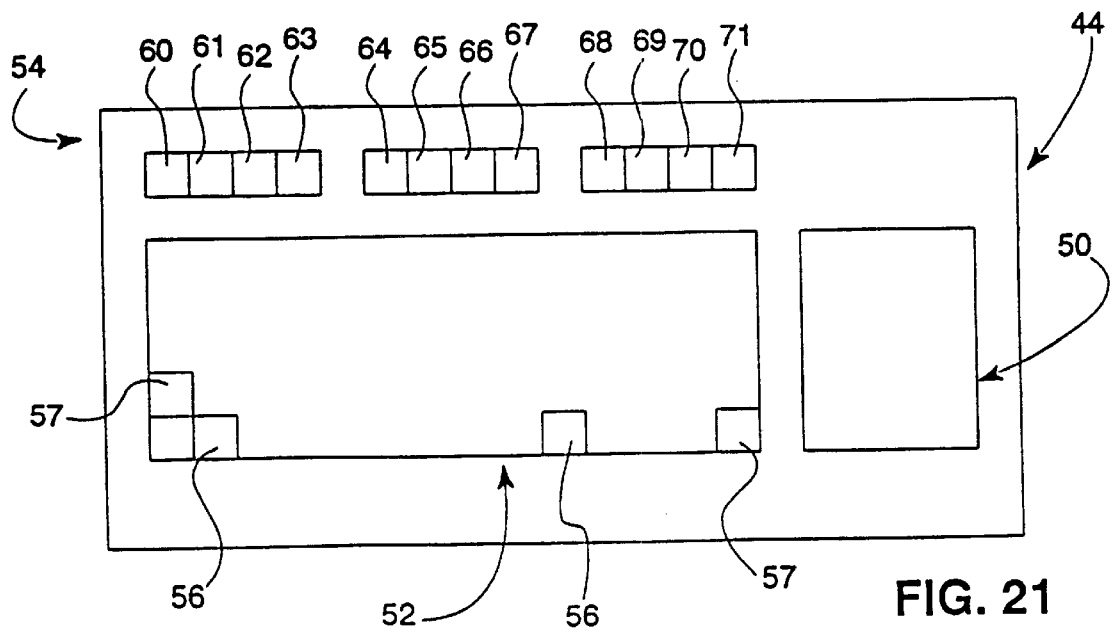
FIG. 21 is a diagrammatic fragmentary view of a system monitor illustrating an application screen and its soft and hard function key templates related to the keyboard of FIG. 20.

In operation, each of the function keys 60–71 can perform two functions in the system 10, either a soft function key function or a hard, function key function. In this regard, as best seen in FIG. 21, both the hard and soft functions of the function keys 60–71 are displayed on each application screen, such as an application screen 80. Navigating between system applications is performed by the user via the hard function keys 60–71. The function of each individual hard function key is pre-determined and is dependent on the environment.

Thus, for example, to access a clinical flowsheet/screen like a vital signs flowsheet, (not shown) the user actuates in combination the F1 function key 60 and an ALT key 56 or a CTRL key 57 on the keyboard 44. This combined action causes the vital signs flowsheet to appear on the monitor 42.

To assist the user in distinguishing the hard function from the soft functions, the functions of hard function keys are displayed in reverse video. For clarity purposes, the reverse video is illustrated merely as shading in FIG. 21.

In summary then, each applications screen such as the application screen 80, includes a soft function key template indicated generally at 82 and a hard function key template indicated generally at 84. Each of the respective soft and hard function key templates 82, 84 includes a series of labels, such as a label 83 and a label 85, respectively. Such labels are indicative of the functions associated with their keyboard function keys 71 and 63 respectively.

To facilitate easy in selecting the correct function key, the soft key template 82 configuration and the hard key function key template 84 configuration correspond to one another. In this regard, each is divided into three groups such as soft function key groups 73–75 where each group has four associated key functions.

For the purpose of clarity hereinafter, the specific functions associated with the function keys 60–71 will not be illustrated as they change according to the environment. In this regard, reference will only be made to F1 through F12. Also for clarity purposes, only the soft function key template will be shown with the general function labels F1–F12. It should be understood however, that each screen produced by the system 10 includes a display of both soft function keys and hard function keys.

C. System Computer Software

The various programs for carrying out the operations of the system 10 can best be understood by reference to the flowchart diagrams of FIGS. 2–13. FIGS. 2–13 illustrate the sequence of operations carried out by the system 10 and any one of its computer processors such as the computer processor 40 in response to input signals received from its associated keyboard 44. Although the input signals are generated by a keyboard, those skilled in the art will understand other input devices, such as a touch screen grid (not shown), a mouse (not shown), or a track ball (not shown) can generate such input signals.

Included in FIGS. 2–13 are separate subroutines which may be called at various times during the operation of the system.

Considering now the CHARTING subroutine 300 in greater detail with reference to FIG. 3, the CHARTING subroutine 300 begins at a start instruction 301 which is initiated from the call instruction 204 in the MAIN program 200.

From the start instruction 301, the flowsheet proceeds to a decision instruction 303 which determines whether a system user requires the system to perform any one of the previously mentioned general administrative functions, such as patient admission or discharge functions. If so, the program advances to a call instruction 304 which causes an ADMINISTRATION subroutine to be called for executing the general administrative functions.

If at decision instruction 303 it is determined that the system user does not desire to use the system to perform administrative functions, the system program goes to a decision instruction 305. At decision instruction 305, a determination is made whether the system user needs to perform an order administration function. If so, the program advances to a call instruction 306 which causes the ORDER subroutine to be called. The ORDER subroutine is beyond the scope of the present invention and will not be described in greater detail.

After the ADMINISTRATION subroutine is executed, the program advances to the decision instruction 305 and proceeds as described previously.

At instruction 305, if it is determined the system user does not desire to perform an order administration function, the program proceeds to a decision instruction 307 which determines whether the system user desires to perform any general flowsheet charting functions such as a flowsheet review or basic function. If so, the program goes to a call instruction 308 which causes the GENERAL CHARTING subroutine 900 to be called. The GENERAL subroutine 900 (FIG. 9) will be described in greater detail hereinafter.

After the GENERAL CHARTING subroutine 900 is executed, the program advances to a decision instruction 309.

At decision instruction 307, if it is determined that the system user does not desire to perform any general flowsheet functions, the program next goes to the decision instruction 309.

At decision instruction 309, a determination is made whether the system user needs to perform any special flowsheet charting functions, such as critical care path functions and integrated charting functions. If so, the program advances to a call instruction 310 which causes a SPECIAL FLOWSHEET CHARTING subroutine 400 to be called. The SPECIAL CHARTING subroutine 400 will be described hereinafter in greater detail.

If it is determined at decision instruction 309 that the system user does not require the system to perform any special flowsheet functions, the program goes to a decision instruction 311 which determines whether any note application functions are required. If so, the program next executes a call instruction 312 which causes an APPLICATION subroutine to be called. The APPLICATION subroutine is beyond the scope of the, present invention and will not be described in greater detail.

After the SPECIAL FLOWSHEET subroutine 400 is executed, the program advances to the decision instruction 311 and proceeds as described previously.

If the system user does not need to perform any note application functions, the program goes to decision instruction 313 from decision instruction 311. The decision instruction 313 determines if the user is requesting any other charting functions. If so, the program returns to decision instruction 303 and proceeds as described previously. If not, the program goes to an exit instruction 314 which returns the program to the MAIN program 200 at decision instruction 205. The program then proceeds from decision instruction 205 as described previously.

Figure 4:
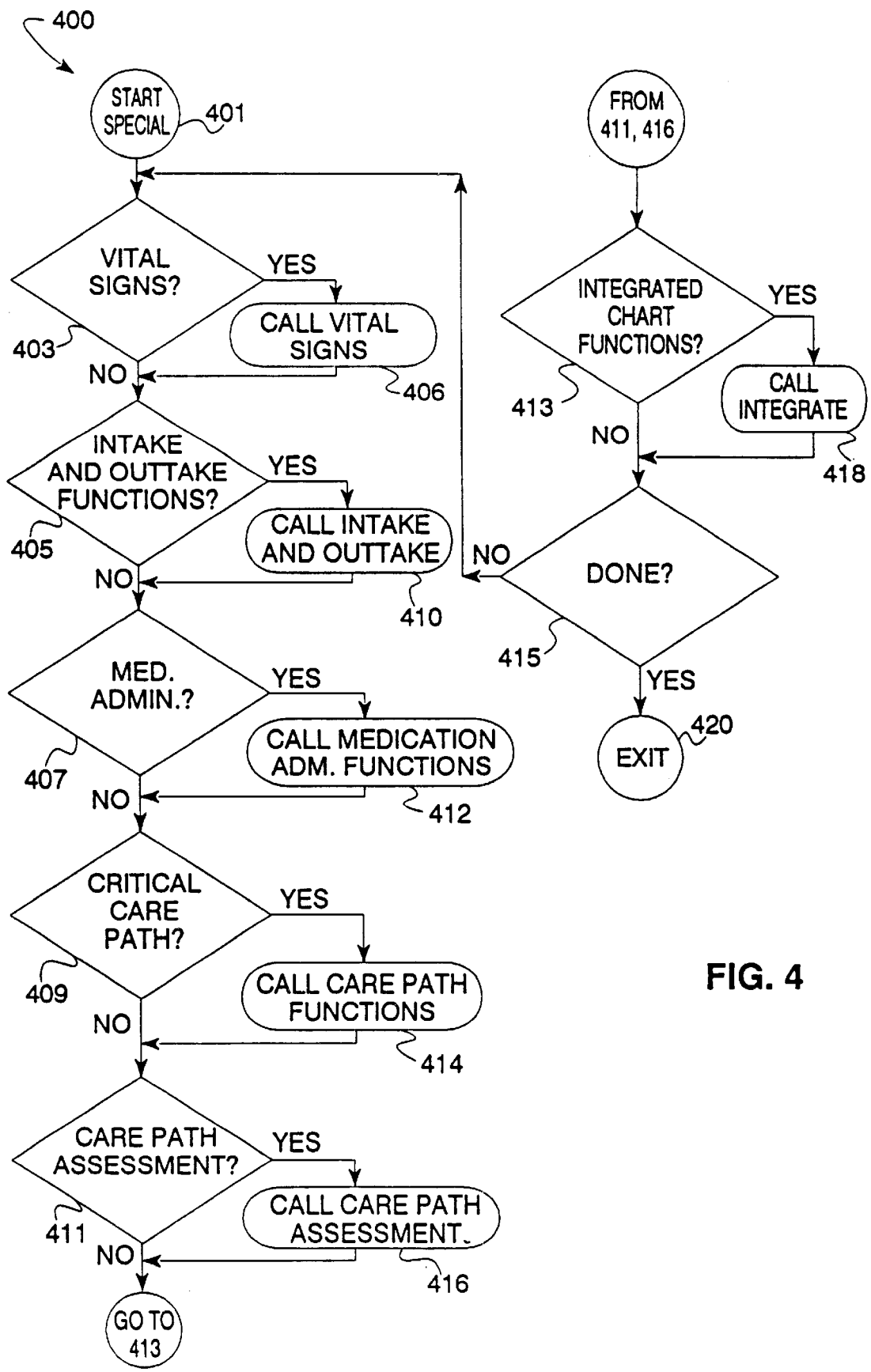

Considering now the SPECIAL FLOWSHEET CHARTING subroutine 400 in greater detail with reference to FIG. 4, the SPECIAL CHARTING subroutine 400 begins at a start instruction 401 which is initiated from the call instruction 310 in the CHARTING subroutine 300 (FIG. 3). From the start instruction 401, the program proceeds to a decision instruction 403 which determines whether a system user requires the system to perform any vital sign function charting. If so, the program proceeds to a call instruction 406 that calls a VITAL SIGNS subroutine. The VITAL SIGN subroutine is beyond the scope of the present invention and will not be described in greater detail.

If the system user does not require the system to perform charting of vital functions, the program next proceeds to a decision instruction 405 which determines whether the user requires the system to perform any fluid intake/outtake charting functions. If so, the program proceeds to a call command 410 which causes an INTAKE/OUTPUT subroutine to be called. The INTAKE/OUTPUT subroutine is beyond the scope of the present invention and will not be described in greater detail.

After the VITAL SIGN subroutine is executed, the program advances to the decision instruction 405 and proceeds as described previously.

If it is determined at decision instruction 405 that the user does not require the performance of any intake/outtake functions, the program advances to a decision instruction 407 which determines whether the system user requires any medication administration charting functions to be executed. If so, the program proceeds to a call instruction 412 which causes a MEDICATION subroutine to be called. The MEDICATION subroutine is beyond the scope of the present invention and will not be described in greater detail.

If no medication charting functions are required, the program goes to a decision instruction 409 which determined whether a critical care path function needs to be performed. If so, the program advances to a call instruction 414 that calls a CRITICAL CARE PATH subroutine 500 that will be described hereinafter in greater detail.

After the MEDICATION subroutine is executed, the program advances to the decision instruction 409 and proceeds as described previously.

At decision instruction 409, if it is determined that no critical care path functions are required, the program goes to a decision instruction 411 which determine as whether a care path assessment is required. If so, the program goes to a call instruction 416 which causes a CARE PATH ASSESSMENT subroutine to be called. The CARE PATH ASSESSMENT subroutine is beyond the scope of the present invention and will not be described except to mention it enables the system user to review and chart by exceptions.

At decision instruction 411 if it is determined no care path assessment functions are to be performed, the program goes to a decision instruction 413 which determines whether any integrated chart functions are to be performed.

After the CARE PATH ASSESSMENT subroutine is executed, the program goes to the decision instruction 413 and proceeds as described previously.

If at decision instruction 413 it is determined that no integrated chart functions are required, the program goes to a decision instruction 415 to determine whether any other charting functions are required. If not, the program proceeds to an exit command 420 which returns the program to the CHARTING subroutine 300 at the decision instruction 311 (FIG. 3) and proceeds as described previously. If other charting functions are required, the program returns to the decision instruction 403 and proceeds as described previously.

At decision instruction 413 it is determined that an integrated client function is required, the program goes to a call instruction 418 which cause a subroutine INTEGRATE to be called. The INTEGRATE subroutine is beyond the scope of the present invention and will not be described in greater detail.

After the INTEGRATE subroutine has been executed, the program proceeds to the decision instruction 415 and proceeds as described previously.

Figure 5:
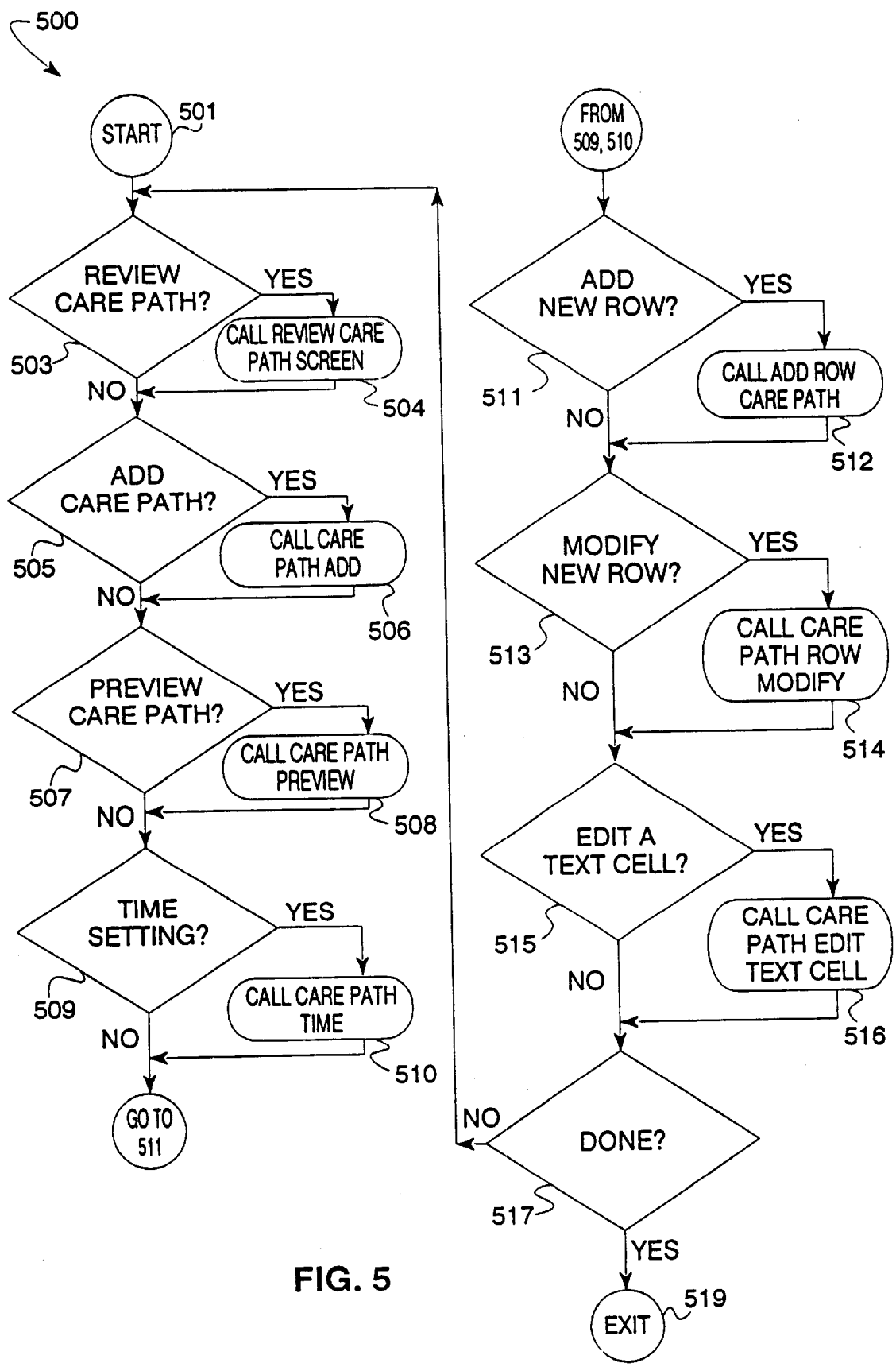

Considering now the CRITICAL CARE PATH subroutine 500 in greater detail with reference to FIG. 5, the CRITICAL CARE PATH subroutine 500 begins at a start instruction 501 which is initiated by the call command 414 in the SPECIAL FLOWSHEET subroutine 400 (FIG. 4). The program then proceeds to a decision instruction 503 which determines whether a system user requires the system to review a care path. If so, the program proceeds to a call instruction 504 that calls a REVIEW CARE PATH subroutine 700. The REVIEW CARE PATH subroutine 700 will be described in greater detail.

If the system user does not require the system to review a care path function, the program next proceeds to a decision instruction 505 which determines whether the user requires the system to perform an add care path function. If so, the program proceeds to a call command 506 which causes an ADD CARE PATH subroutine 600 (FIG. 6) to be called. The ADD CARE PATH subroutine 600 will be described in greater detail.

After the REVIEW CARE PATH subroutine 700 is executed, the program goes to the decision instruction 505 and, proceeds as described previously.

If it is determined at decision instruction 505 that the user does not need to add a critical care path, the program advances to a decision instruction 507 which determines whether the system user requires the preview of any care path. If so, the program proceeds to a call instruction 508 which cause a CARE PATH PREVIEW subroutine to be called. The CARE PATH PREVIEW subroutine is beyond the scope of the present invention and will not be described hereinafter in greater detail.

If no care path preview functions are required, the program goes to a decision instruction 509 which determines whether any time setting functions needs to be performed. If so, the program advances to a call instruction 510 that calls a CRITICAL CARE PATH TIME subroutine. The CRITICAL CARE PATH TIME subroutine is beyond the scope of the present invention and will not be described hereinafter in greater detail.

At decision instruction 509, if it is determined that no critical care path timing functions are required, the program goes to a decision instruction 511 which determines whether a new row needs to be added to a selected care path chart. If so, the program goes to a call instruction 512 which causes an ADD CARE PATH ROW subroutine 1300 (FIG. 13) to be called. The ADD CARE PATH ROW subroutine 1300 will be described in greater detail hereinafter.

At decision instruction 511, if it is determined that no add row functions are to be performed, the program goes to a decision instruction 513 which determines whether any row modifications function are to be performed. If so, the program advances to a call instruction 514 which causes a MODIFY subroutine 1200 (FIG. 12) to be called. If not, the program goes to a decision instruction 515 to determine whether any editing functions are required. After the MODIFY subroutine 1200 is executed, the program goes to the decision instruction 515 and proceeds as described previously.

At decision instruction 515, if it is determined no editing functions are required, the program proceeds to a decision instruction 517 which determines whether any other critical care path functions are to be performed. If so, the program returns to decision instruction 503 and proceeds as described previously. If not, the program goes to an exit command 519 which returns the program to the SPECIAL FLOWSHEET subroutine 400 (FIG. 4) at decision instruction 411 where the program proceeds as described previously.

If at decision instruction 515, it is determined an edit function is to be performed, the program goes to a call instruction 516 which causes an EDIT subroutine 1100 (FIG. 11) to be called. The EDIT subroutine 1100 will be described hereinafter in greater detail.

After the EDIT subroutine 1100 has been executed, the program advances to the decision instruction 517 and proceeds as described previously.

Figure 7:
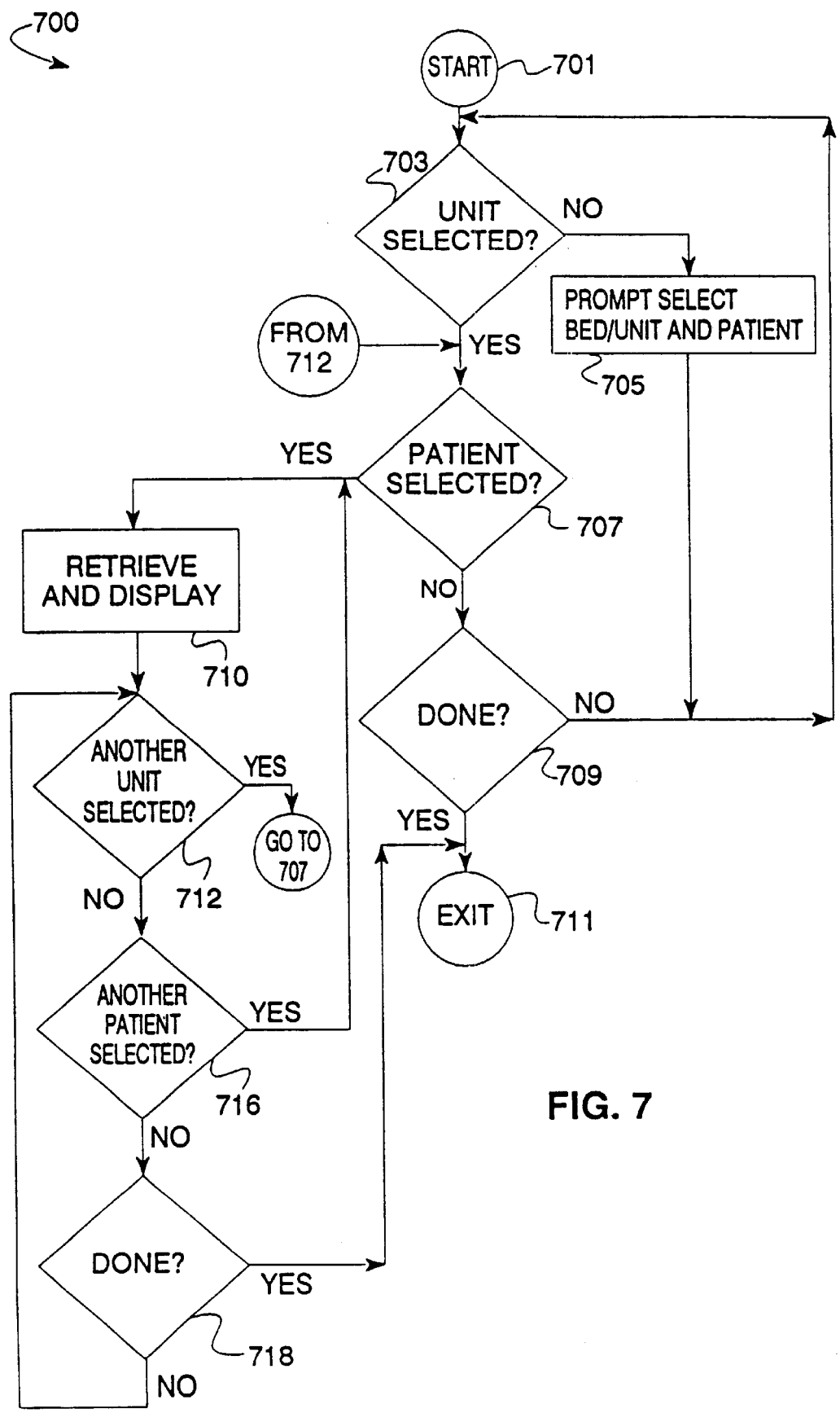
Figure 8:
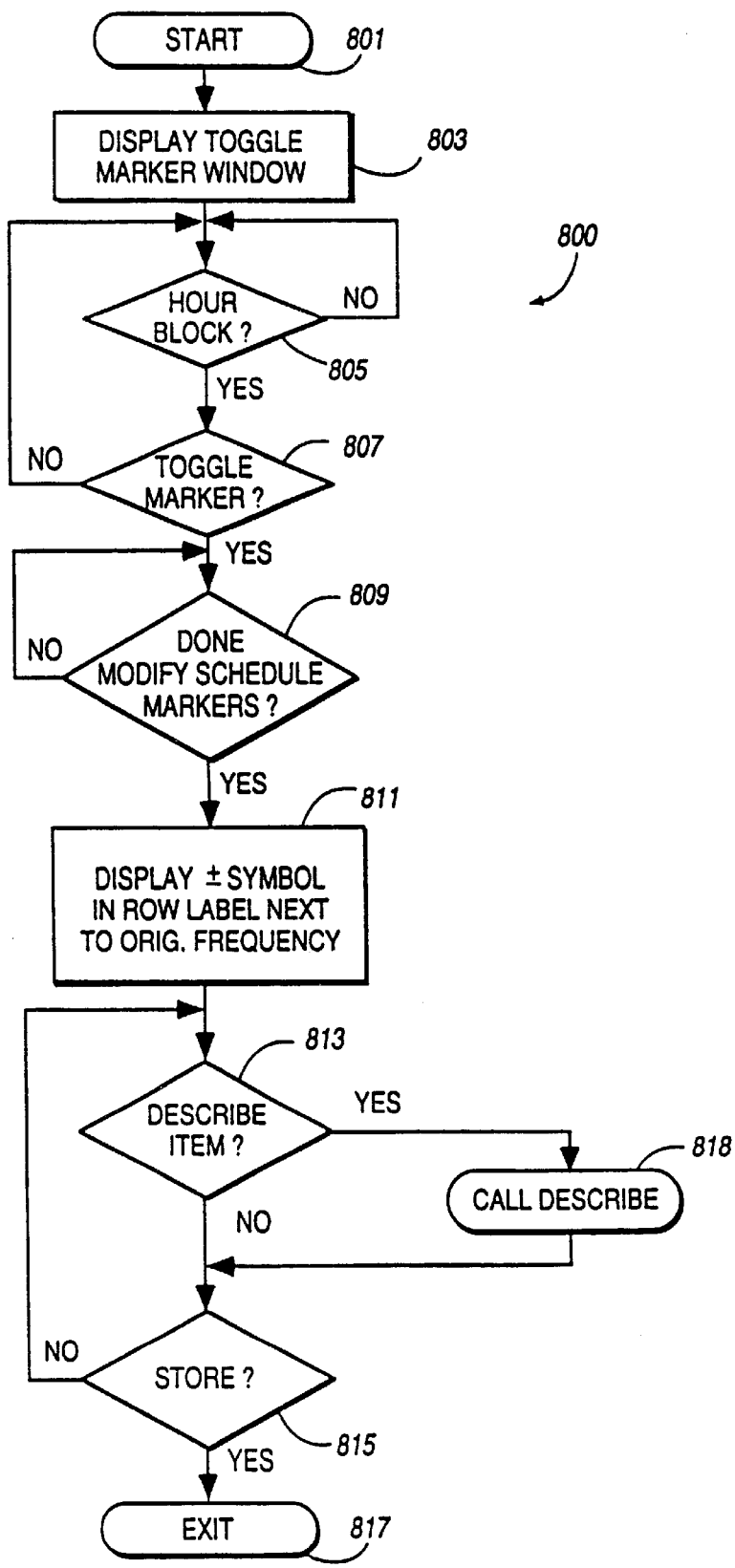
Figure 9:
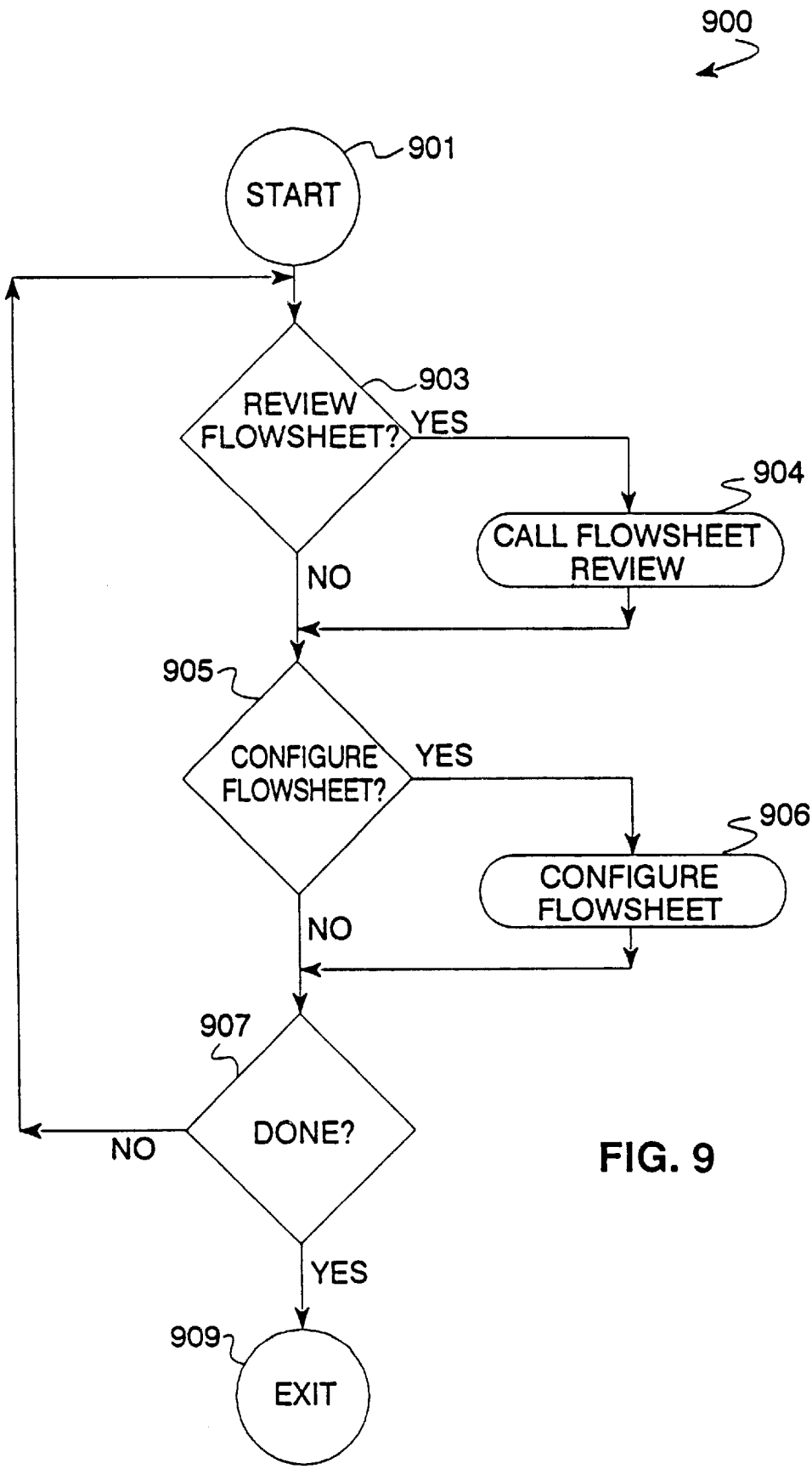

Considering now the REVIEW CRITICAL CARE PATH subroutine 700 in greater detail with reference to FIG. 7, the REVIEW CRITICAL CARE PATH subroutine 700 begins at a start instruction 701 which is initiated from either the call command 504 (FIG. 5) or the call command 904 in the subroutine 900 (FIG. 9). In this regard, each display station location, such as the display station 14A is programmed to default to patient control screen (not shown) where the display station is located. By using the appropriate function keys, the default screen can be caused to be displayed on the monitor 25.

To select a unit, the user moves the cursor to highlight a desired unit and depress the enter key on the keyboard 24. In this regard, the program proceeds to a decision instruction 703 which determines whether the system user has selected a care unit. If not, the program goes to a command instruction 705 which causes a prompt to be displayed requesting the user to select a bed/unit and patient. The program then returns to the decision instruction 703 and proceeds as described previously.

After the user selects a bed unit, the program advances from the decision instruction 703 to a decision instruction 707 which determines whether the user has selected a patient. If not, the program goes to a decision instruction 709 to determine whether the user is done with his or her review. If so, the program proceeds to an exit command 711 which terminates the review subroutine 700.

If the user has not completed his or her review, the program goes from the decision instruction 709 to the decision instruction 703 and proceeds as described previously.

When the user selects a patient, the program goes from the decision instruction 707 to a command 710 which causes the selected patient information to be retrieved and displayed. The program then goes to a decision instruction 712 which determines whether the user desires to review a care path in another unit. If so, the program goes to decision instruction 707 and proceeds as described previously. If not, the program advances to a decision instruction 716 which determines whether the user desires to select another patient in the unit presently selected.

If the user selected another patient in the same unit, the program returns to the command 710 and proceeds as described previously.

If the user has not selected another patient, the program proceeds to a decision instruction 718 which determines when the user has completed his or her review. In this regard, when the user Completes the review, the program goes to the exit command 711 and proceeds as described previously. If the review has not been completed, the program goes to the decision instruction 712 and proceeds as described previously.

From the foregoing, it should be understood a selected critical care path screen will he retrieved and displayed, such as the critical care path screen 1400 (FIG. 14).

Figure 15:
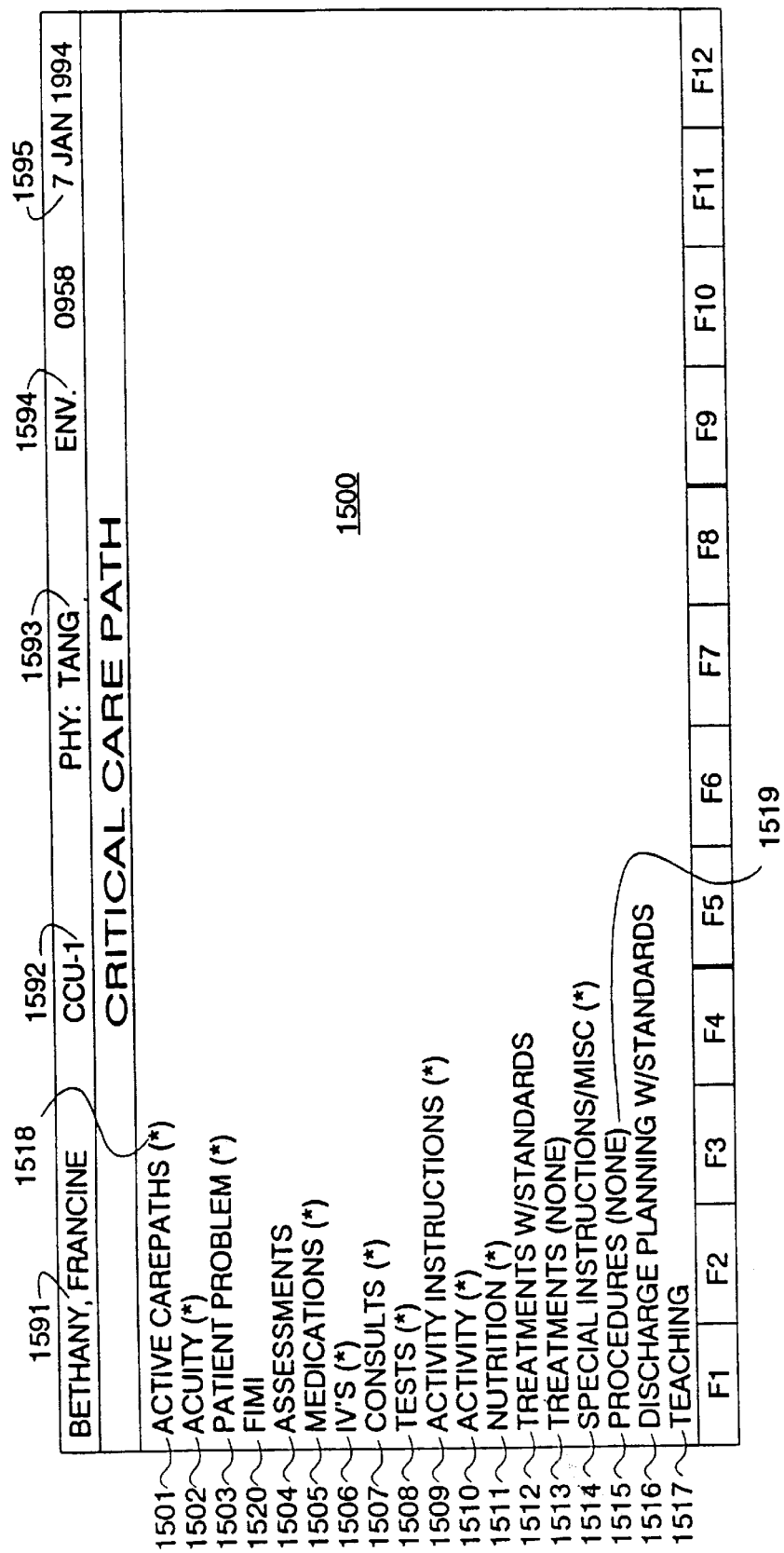
FIG. 15 illustrates a critical care path screens generated by the system at FIG. 1.

Considering now the clinical information system 10 in still greater detail, and more specifically critical care path charting, as best seen in FIG. 15, whenever a healthcare provider desires to perform any one of a plurality of different critical care path functions relative to a given patient, the provider can select the patient and request that a given monitor display the critical care path information for the selected patient. In this regard, a screen 1500 will be displayed on the user active monitor, such as the monitor 25 at display station 21.

The critical care path screen 1500 is menu driven and displays for the user a plurality of different critical care path flowsheet items. Such flowsheet items may include, for example, active care paths (*)1501, acuity (*)1502, patient problem (*)1503, assessments 1504, medications (*)1505, IV's (*)1506, consults (*)1507, tests (*)1508, activity instructions (*)1509, activity 1510, nutrition (*)1511, treatments with standards 1512, treatments (none) 1513, special instructions/misc (*)1514, procedures (none) 1515, discharge planning w/standards 1516, teaching 1517, FIMI 1520 or others (not shown).

The appearance of "(*)" indicia, such as the indicia 1518 is indicative that the flowsheet contains charted patient data. The appearance of "(none)" indicia, such as the indicia 1519 is indicative that there are no row items in flowsheet.

Whenever the user highlights one of the flowsheet items, such as the active care paths (*) item 1501 and activates the enter key on the user active keyboard, such as the keyboard 24 at display station 21, an associated drop down window will appear on the monitor screen, such as a drop down active care path (*) window 1696 (FIG. 16) or a drop down patient problem (*) window 1697 (FIG. 16). Whenever a drop down window appears on the monitor screen, such as the screen of monitor 25, the remaining displayed flowsheet items may be shifted off screen. By using the arrow up and down keys on the keyboard 24, different flowsheet items may be brought to the screen to be activated.

As will be discussed in greater detail, a critical care path is a diagnosis specific, multi-discipline, time sequenced patient care plan. In this regard, the information in any given critical care path is formed for each patient by adding care paths that have been defined by preexisting hospital Standards of Care. The preexisting hospital Standards of Care once added to a critical care path can then be tailored to each patient's need and expected outcomes. Thus, a visual indication of the status of a patient can be seen on a critical care path assessment flowsheet (not shown) upon activating the assessments flowsheet item. Such documentation is in accordance with the primary care facility Care Path Assessment protocol and Standards of Care, or alternately by using a standard clinical information system flowsheet.

The critical care path screen, such as the screen 1400 (FIG. 14A), or the screen 1600 (FIG. 16) provides a healthcare provider, administrator, nurse, physician or other interested person with a visual indication of a patient care plan. The critical care path screen 1600 is formed for each patient by adding care paths that have been defined by the hospital pre-existing Standards of Care treatments and procedures. As will be explained in greater detail, a given care path is a diagnosis specific, multi-discipline, timed-sequenced patient care plan that is tailored to the needsand expected outcomes of each patient. Patient status can be documented on a CBE Flowsheets (not shown) in accordance with the CBE protocol and Standards of Care established by a given hospital or alternately, by using a CIS flowsheet.

For example, referring to FIG. 16, a given patient care path screen 1600 includes an active care path select 1601, a time schedule 1603, and a user-defined task section 1607. The active care path section 1601 has one or more active care paths, such as a single active care path indicated generally at 1696. In this regard, the care path is for a hip replacement. The time schedule or time line indicated generally at 1602 provides the user with a date 1603 the patient is admitted to the hospital and a date 1605 the patient will undergo surgery. The textual section 1606 includes textual data below the dates 1603 and 1605 describe the appropriate active, e.g. "pre-op day 1" and "operative day" respectively.

The active care path section 1601 defines care paths for surgical diagnoses which are configured for pre and post surgery patient care, such as a hip replacement procedure. The active care path section 1601 also defines care path for medical diagnoses which are configured for non-surgical patient care. For example, a patient may be admitted to a primary care facility for a hip replacement surgical procedure and who has also been diagnosed as being a diabetic, or having pneumonia. For example, in FIG. 14A, a critical care path has two active care paths, such as a hip replacement care path 1430 and a pneumonia evaluation care path 1440, will be assigned to such a patient to track the surgical diagnosis hip replacement care path 1430 and the medical diagnosis pneumonia care path 1440.

From the foregoing, it should be understood by those skilled in the art that based on the medical diagnosis of the patient, the user can select pre-configured care paths to appear automatically on a critical care path screen. The screen can then be tailored by merging several care plans to account for different diagnoses and multiple operations as will be explained in greater detail.

In operation, when the hip replacement active care path is selected by the user, the system 10 causes a group 1698 of standard care items to be displayed. For example, the group 1698 includes four standard of care items a bowel elimination item 1610, a comfort item 1620, a knowledge deficit item 1630 and a mobility impaired physical item 1640. Corresponding text cells are associated with each of the standard of care items, such as cells 1611–1618.

The text cells include excepted outcome information for the active care path. Such information can be modified at any time. In this regard, the information can be modified before actual patient treatment, during treatment upon the occurrence of an exception or the necessity of adding another active care path.

As will be explained in greater detail, the information in a text cell will be repeated from date to date or until modified by the system user. A system user may also discontinue the repeated information at any date selected by the user.

From the foregoing, it should be understood by those skilled in the art that editing of the text cells allows the user to easily customized the critical care path for any given patient.

Information in the individual text cells will not be changed until such time as a system user adds information or modifies information contained in a cell. In this regard, if the patient responds to the normal expected standard of care outcomes, no textual information will be required.

If a given patient experiences a problem, the user may add text to an expected to expected problems, outcomes, or the status of a patient. Cells 1614–1618 for example provide such textual information.

The methods of adding rows, adding or modifying Cell text, adding additional care paths and adding and modifying care paths configurations will be described hereinafter.

1. Add Care Path

Figure 6:
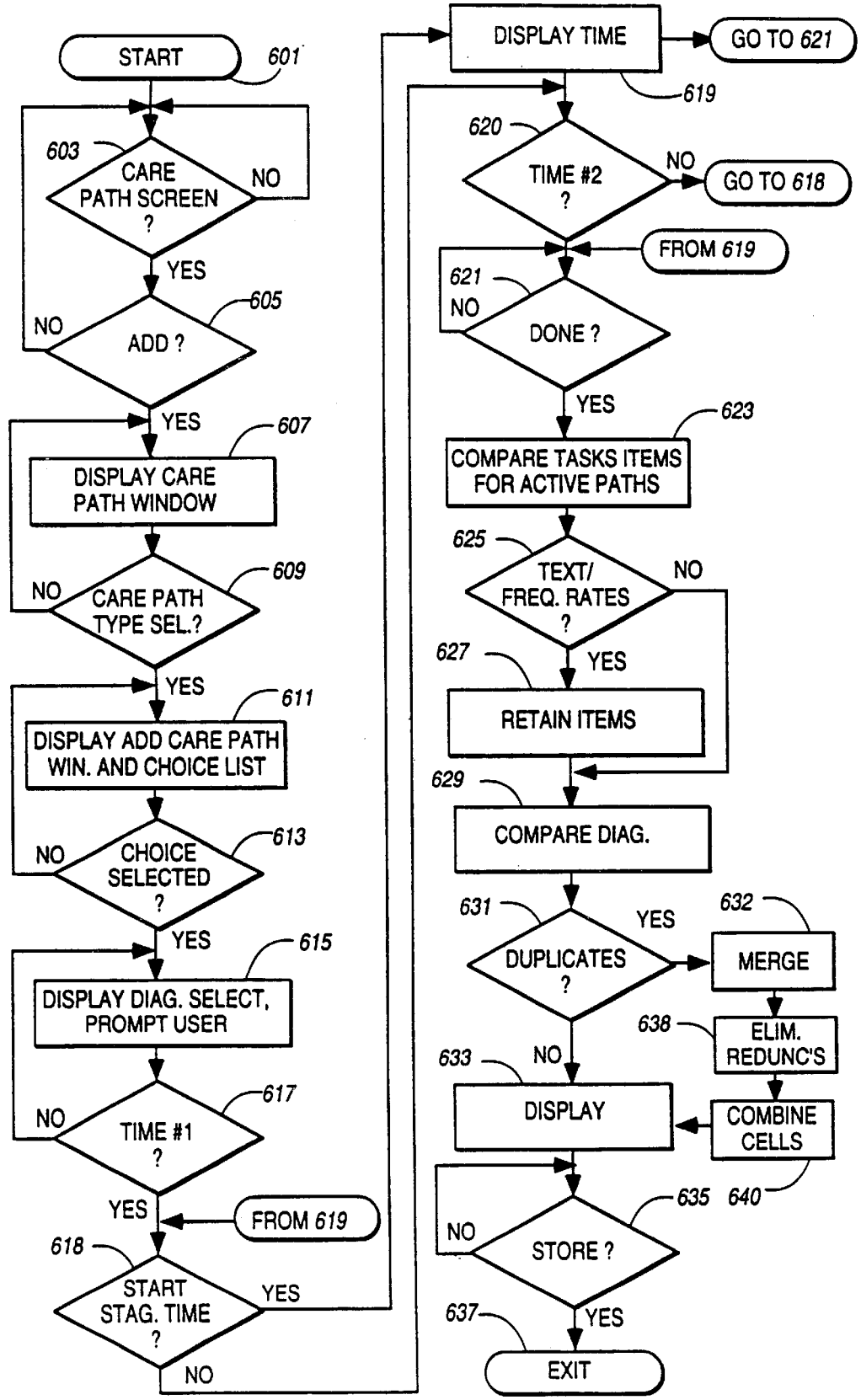

Considering now the ADD CARE PATH subroutine 600 in greater detail with reference to FIG. 6, the ADD CARE PATH subroutine 600 begins at a start instruction 601in response to the call command 506 from the CRITICAL CARE PATH FLOWSHEET CHARTING subroutine 500. In this regard as noted earlier, based on the medical and surgical diagnosis of a patient, a system user can select pre-configured CARE PATHS to appear automatically on the CRITICAL CARE PATH SCREEN, such as on a screen 1600 in FIG. 16. Once the Care Path Screen is displayed, the user can then tailor its entries by merging several CARE PATHS to account for different diagnoses and multiple operations.

Those skilled in the art will understand that all care paths are defined by the administration of the primary care facility according to existing Standards of Care. Such Standards of Care contain text items such as the text indicated in text item section 1606 and tasks such as the tasks in the user-defined task section 1607.

The text item section 1606 includes textual information which is based on the selected care path. Such information defines the expected outcomes over a given period of time defined by a plurality of time columns, such as time columns 1603 and 1605. The textual information can be changed on a per cell basis for individualized patient care as will be explained hereinafter.

Considering now the CRITICAL CARE PATH SCREEN 1400 in greater detail with reference to FIG. 14A, screen 1400 includes an active care path section 1401, and a text item section 1403 having one or more primary text cells, such as a primary text cell 1411–1412 and one or more secondary or repeat text cells, such as a repeat text cell 1415–1418.

The primary text cell 1411 is the initial cell where textual information is stored. The text which appears in this cell will automatically be reproduced in the secondary cells 1415 and 1417. In order to distinguish between thee primary cells from the repeating cells, each primary cell is preceded by a shaded vertical bar, such as a vertical bar 1413 associated with the primary cell 1411 and a vertical bar 1414 associated with a primary cell 1412 to distinguished it from a secondary cell, such as cells 1415 and 1416, respectively.

The secondary or repeating cells, such as repeating cells 1415 and 1416 contain duplicate text from their respective primary cells 1411 and 1412. A secondary cell, such as the secondary 1415 can be modified to contain textual information which is different than that associated with the primary cell 1411. In this event, another vertical bar (not shown) would appear before the modified cell so that it becomes a primary cell as opposed to a secondary cell.

FIG. 14B illustrates another critical care path screen 1420 which is substantially similar to screen 1400 (FIG. 14A) except that it includes an expected outcome window, indicated generally at 1425 which is superimposed over an acuity active care path 1421 and a patient problem care path 1422. As will be explained hereinafter in greater detail, configured expected outcomes appear in the critical care path screen, such as in the screen 1420 whenever the system user activates an expected outcome soft function key, such as a soft function key F11. The expected outcomes can be entered and modified via the F11 function key. The information on each care path item will differ per the item type section when the "Describe Item" soft function key is activated, such as the F7 function key. In this regard, for the "Active Care Path" section 1401, all values of the assigned care path will appear and in the text section 1403, all item information and comments will appear.

Figures 14D, 14E, 14F, 14G:
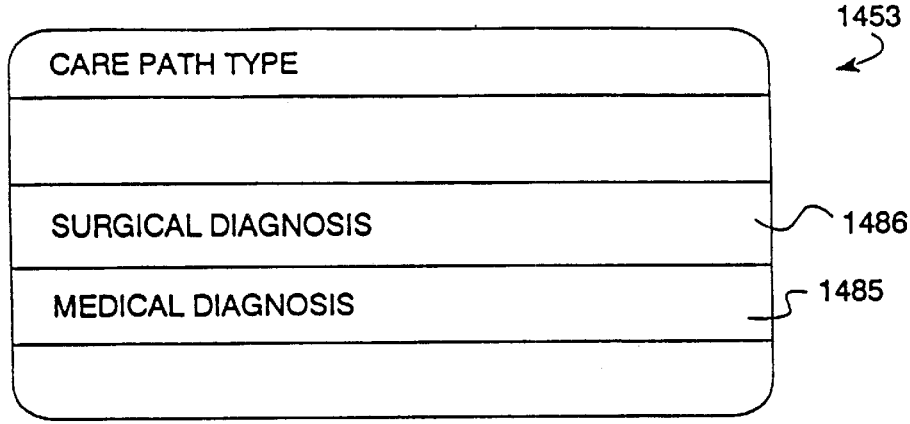
FIGS. 14D–E illustrate windows which may appear on the screen of FIGS. 14A–C
FIGS. 14F–G illustrate windows which may appear during creation and modification of database configurations.

To add a CARE PATH, the new user first selects a CRITICAL CARE PATH SCREEN for a given patient, such as the CRITICALCARE PATH SCREEN 460 (FIG. 14C). Next, the user causes the screen cursor (not shown) to be positioned to an ACTIVE CARE PATH section, such as the ACTIVE CARE PATH section indicated generally at 1461. The user then activates an ADD CARE PATH function key, such as the soft function key F3 which causes a CARE PATH TYPE WINDOW 1453 (FIG. 14D) to appear on the ADD CARE PATH SCREEN 1460.

Using an Up arrow or Down arrow key on the keyboard 44, the user causes the desired CARE PATH TYPE to be accented or highlighted. Such highlighting is indicative of the choice of the user. Next, the user depresses the Enter key (not shown) on the keyboard 44 to cause an ADD CARE PATH WINDOW 1484 to appear on the screen 1460. The ADD CARE PATH WINDOW 1484 is indicative of the selected CARE PATH TYPE, such as a medical diagnosis type 1485 or a surgical diagnosis type 1486 (FIG. 14D) which corresponds, for example, to a case of pneumonia or hip replacement surgery, respectively.

When the window 1484 appears, the user selects and types in a choice list number which corresponds to the desired CARE PATH. A choice list 1462 appears in the window 1484 when the number is entered, the system responds by displaying the care path type and care path name in a predefined CARE PATH TYPE area 1487 and a predefined CARE PATH name area 1488, respectively.

Depending upon the type of diagnosis or care path selected, the user is prompted to enter a start time or an evaluation time. In this regard, the window 1484 includes a predefined area 1463 for entry of the evaluation time or start time. The start time or evaluation time is required to activate the selected CARE PATH.

Also, depending upon the CARE PATH TYPE, the user will. enter in another predefined area 1464 of the window 1484 either a stabilization time or a post-op time, if known.

When the user has completed entry of the information to add a CARE PATH, he or she activates the Done function key, such as the soft function key F3, which in turn causes the new care path, such as path 1440 (FIG. 14A) and corresponding Text and Task items to automatically appear in the applicable sections on the CRITICAL CARE PATH SCREEN, such as the screen 1400.

Any patient specific customization is performed at this time. As will be explained herewith in greater detail, once information entered in a given row is stored, neither row labels nor the rows themselves may be deleted. Cells which define periods of time within any row, however, may be modified.

When the selected CARE PATH is merged with the other CARE PATHS in a given CARE PATH SCREEN, the new items will be combined with existing items on both the CARE PATH SCREEN and the CARE PATH ASSESSMENT FLOWSHEET. Text sections, however, are not merged and any duplicate diagnoses are displayed alphabetically. Also, if a frequency is present, task items will not be merged. In this regard, the user can customize the CARE PATH SCREEN for duplicate diagnoses and task items having the same or different frequencies.

When the user completes any customization, he or she activates a store function key 1471, which in turn, causes the system to store the CARE PATHS.

Referring again to FIG. 6, after the start command 601 is executed, the program proceeds to a decision instruction 603 to determine whether the system user has selected a CARE PATH SCREEN, such as the screen 1460. If not, the program loops at 603 until the user selects a screen.

When the user selects a CARE PATH SCREEN, the program advances to a decision instruction 605 which determines the user hag selected the ADD CARE PATH function. If not, the program returns to instruction 603 and proceeds as described previously.

If the user has selected the ADD CARE PATH function, the program goes to an instruction command 607, which causes a CARE PATH WINDOW to be displayed, such as the CARE PATH window 1461 to be displayed on the critical care path screen, such as the screen 1460.

Next, the program advances to a decision instruction 609 which determines whether the user has selected a CARE PATH TYPE. If not, the program loops at 609 until a CARE PATH TYPE has been selected by the user.

When the user selects the desired CARE PATH TYPE, the program proceeds to a command instruction 611, which causes the selected ADD CARE PATH window to be displayed, such as the window 1484.

The next program goes to a decision instruction 613 which determines whether the user has selected a choice item from the displayed choice list 1462 (FIG. 14E). If not, the program waits at instruction 613 until the user enters a choice item number.

After the user enters a choice item number, the program advances to a command instruction 615 which causes selected diagnosis CARE PATH to be displayed in the care path type area 1487 and the care path name area 1488 respectively and prompts the user to enter either the time or the evaluation time, depending upon the type of CARE PATH selected by the user.

The program proceeds to a decision instruction 617 which determines if the user has entered the evaluation time. If not, the program loops at instruction 617 until the evaluation time is entered.

The program then goes to the decision instruction 618 which determines whether the user has entered the start stabilization time, if known. If the user enters a time, the program advances to a instruction 619 which causes the time to be displayed. The program then proceeds to a decision instruction 621 which determines whether the user has completed entering the requested information.

If the user did not enter a stabilization start time at decision instruction 618, the program goes to another decision instruction 620 to determine if the user entered an evaluation time. If not, the program returns to the decision instruction 618.

If the user enters an appropriate evaluation time, the program goes to the decision instruction 621, which determines whether the user is done entering the requested information. If not, the program loops at instruction 621 until the user enters the done function.

When the user enters the done function by depressing the "Done" soft function key F3, the program causes the critical care path flowsheet to be displayed such as the flowsheet 1400. In this regard, the new care path and corresponding text and task items will automatically appear in the applicable sections on the critical care path screen.

The program then goes to a command instruction 623 which compares the CARE PATH just added with all the active CARE PATHS for the selected patient. The program then goes to a decision instruction 625 which determines whether a text box, such as a text box 1702 (FIG. 17) or frequency time is present in the added care path. An example of a frequency time relates to the frequency of a treatment, such as the number of times each day a medication is to be administered. If either a text box merger or a frequency merger is to be performed, the program advances to a command 627 which causes all text box items and all frequency items to be listed. Such duplicate listing of information, such as "knowledge deficit" 1804 and 1805 (FIG. 18) respectively, alerts the healthcare provider/user to analyze the plan for any potential conflicts.

After command instruction 627 is executed, or no text or frequency items are present, the program proceeds to a command instruction 629 which compares the cell information to be merged. The merger of cell information is required to take place. Such a merger involves the merging of two or more lists of information relating to multiple diagnoses. For example, the merger of assessments for each diagnosis takes place by eliminating redundant assessments, so that a combined listing of assessments can be stored. Such a technique is properly performed by the system 10, because no independent human intervention of the healthcare provider is required, unlike the merger performed for text boxes and the frequency of treatment of the patient.

When the diagnoses are compared the program advances to a decision instruction 631 which determines whether there are any duplicate assessment entries. If so, the program proceeds to a command instruction 632 which identifies the redundant assessment items. The program then proceeds to a command instruction 637 which eliminates one of each of the redundant items. Next, the program advances to a command instruction 640 which causes the remaining assessment items to be combined into a single list of items with no redundancies. The program then goes to a command instruction 633 which causes the text, frequency and assessment items to be displayed.

If there are no duplicate assessment items, the program goes directly to command instruction 633. From the command instruction 633, the program goes to a decision instruction 635 which determines whether the user has requested the customized information he or she has entered to be stored. When merging multiple care paths, the new items will be combined with the existing items on the critical care path screen as well as the care path assessment flowsheet. However, the text and frequency sections will not merge and information will be displayed on separate rows. If similar subject matter information exists for two or more task items, such as the knowledge deficit task items 1630 and 1702 in FIGS. 16 and 17 respectively, both items are displayed on different rows such as items 1804 and 1805 as illustrated in FIG. 18, to alert the user to make a decision, if necessary, as to which one of the two items should apply, or if a third approach should be taken at any given time. Therefore, the user will have the opportunity to review potential conflicts at this time, as well as in the future, and to enter any desired customization information.

By way of example to illustrate the merge function for cell information, it is best seen in FIGS. 23–25. FIG. 23 illustrates a critical care path screen 2300 for a patient diagnosed with a surgical hip replacement procedures. In this regard, the screen includes, a hip replacement active care path 2301 and a large number of assessments 2310–2320 associated with the surgical diagnosis.

FIG. 24 illustrates a critical care path screen 2400 for the same patient who has developed pneumonia. In this regard, the screen 2400 includes a pneumonia active care path 2400 and a corresponding large number of assessments 2410–2417.

Under the merge function for merging multiple care paths, screens 2300 and 2400 are merged into a single screen 2500. In this regard, as best seen in FIG. 25, the assessments for the two merged care paths includes only eleven assessment items 2510–2520 as opposed to nineteen assessment items (11 for hip replacement and 8 for pneumonia). The duplicated ones of the assessment items for the pneumonia path have been eliminated. These items are cardiovascular 2410, neurological 2411, respiratory 2412, gastrointestinal 2413, musculoskeletal 2414, neurovascular 2415, psych/social 2416 and pain 2417.

Although not shown in FIG. 6 for clarity purposes, it should be understood by those skilled in the art that the merged active care paths and their associated text cells, task items, and flowsheets can be aborted, deleted, edited, and modified at any time before the user actuates the "store" soft function key. Thus, while FIG. 6 illustrates that the program loops at decision instruction 635, it should be understood that other functions relating to the critical care path screen can be performed.

Considering now the operation of the system 10 with reference to FIGS. 16–18, the following will help facilitate the understanding of the text box merged care paths function. A patient (not shown) diagnosed as requiring hip replacement surgery is admitted to a healthcare facility for surgery. A critical care path screen 1600 that illustrates selected activities relating to the hip replacement active care path 1606 associated with such a patient is shown in FIG. 16.

While confined at the healthcare facility, the patient develops pneumonia. FIG. 17 is a critical care path screen 1700 that illustrates selected activities relating to an active care path 1701 of a medical diagnosis of developed pneumonia.

As explained earlier, the secondary diagnosis of pneumonia (FIG. 17) can be merged or added to the surgical diagnoses illustrated in FIG. 16 using the ADD CARE PATH subroutine. In this regard, when the active care paths are merged a single combined care path screen 1800 (FIG. 18) is created. The combined active care paths 1801 and 1805 include two similar entries illustrated at 1804 and 1805 for task items, namely knowledge deficit. One is for the hip replacement diagnosis 1804, and the other is on the pneumonia diagnosis 1805. These similar entries are listed in an alphabetical order on separate adjacent rows relative to the active care paths. Thus, the text cells are not merged, but are listed as separate text items. Such similar entries facilitate analysis of potential conflicts by the healthcare provider/user, since they are displayed next to one another.

The program waits at decision instruction 635 until the user has entered all of the necessary customization information. When the user is done, the program advances to an exit command 637, which returns the program to the decision instruction 507 in the CRITICAL CARE PATH FLOWSHEET CHARTING SUBROUTINE 500.

It should be noted that the post-operation time or stabilization time may be set after assigning the CARE PATH. The "post-op" time is assigned to a surgical diagnoses and the "stabilization" time is assigned to the medical diagnosis.

To set the appropriate time when known, the user selects the desired CRITICAL CARE PATH SCREEN, such as the screen 1460. The user then moves the cursor to highlight the desired CARE PATH in the ACTIVE CARE PATH SECTION 1461.

Next the user activates a "set post-op" or a set stab function key such as function key F4, which in turn causes an edit post-op screen (not shown) to appear. The user then enters the desired time and activates the enter key.

When the user is finished setting the time, he or she activates the done function key F3. All subsequent time columns for the selected CARE PATH will then appear as either "post-operative day X" or stabilization.

When the user is finished with the entire screen, the user activates the store function key F8.

2. Add New Row

Figure 10:
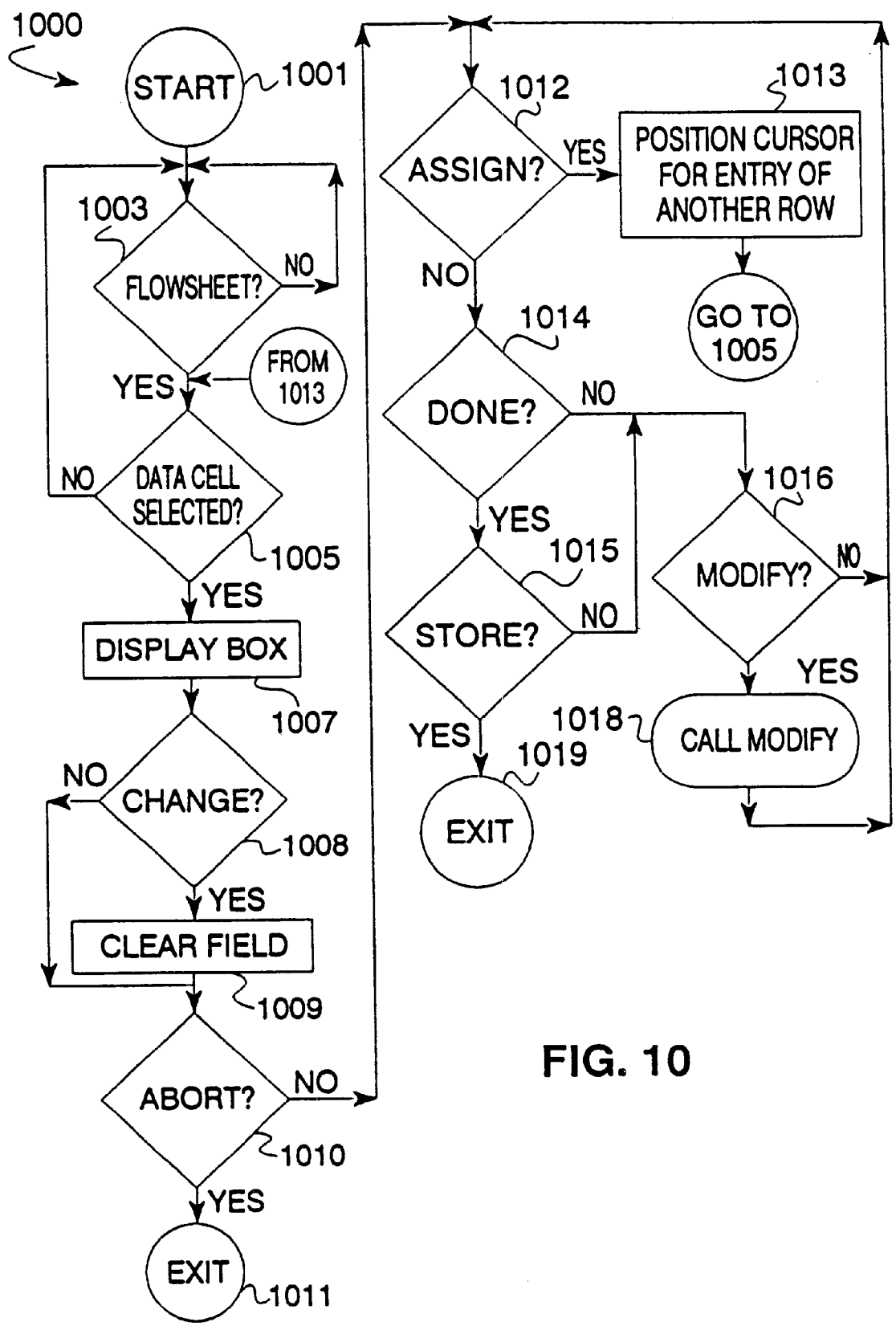

Considering now the ADD NEW ROW subroutine 1000 in greater detail with reference to FIG. 10, when the call command 512 is executed in the CRITICAL CARE PATH subroutine 500, a start command 1001 begins the ADD NEW ROW subroutine 1000.

From the start command 1001, the program advances to a decision instruction 1003 which determines whether the user has selected a critical care path flowsheet. If not, the program loops at decision instruction 1003 until the user makes a flowsheet selection.

When a flowsheet has been selected by the user, the program proceeds to a decision instruction 1005 which determines whether the user has activated a new row soft function key F3 and has positioned the cursor to a desired data cell in the flowsheet. If not, the program returns to decision instruction 1003 until the data cell has been selected.

When the data cell has been selected, a New Row Screen 2200 (FIG. 22) appears for one section type, the section type that was selected by the user. The user is then prompted to enter the requested information which includes a name 2201, a command 2202, a start time 2203 and a discontinue or D/C time 2204.

As the user enters the requested information for each field, the user activates the enter key which advances the screen cursor to the next field.

If the user desires to clear all fields in the new row window 2200 and return to the name field, the user activates the "Clear Fields" soft function key F4.

To abort the new row mode, the user activates the "cancel all" soft function key F12. To clear a default time when in a time filed, the user activates a "clear time" soft function key, such as the soft function key F1.

When the user is entering the information for the new row, the program advances to a decision instruction which determines whether the user desires to change any of the information entered. If so, the program advances to a command instruction 1009 which causes the appropriate field or fields to be cleared.

Next, the program advances to a decision instruction 1010 which determines whether the user desires to abort the new row function. If so, the program goes to an exit instruction 1011 which terminates the new row function.

At decision instruction if the user does not desire to change the entered information, the program proceeds directly to the decision instruction 1010 and proceeds as previously described.

If the user does not desire to abort the new flow function, the program goes to a decision instruction 1012.

At decision instruction 1012, if the user has depressed the "Assign" soft function key F2, the cursor will be positioned automatically for the entry of a new row by the program advances to a command instruction 1013. After command 1013 is executed, the program goes to the decision instruction 1005 and proceeds as described previously.

At decision instruction 1012, if it is determined the user does not desire to add any additional new rows, the program goes to a decision instruction 1014.

At decision instruction 1014, if it is determined the user has completed adding new row information, the program goes to a decision instruction 1015. In this regard, if the user depresses the soft function key F3, the program goes to the decision instruction 1015.

If the user desires to remove a new row before it has been stored, the user positions the cursor on the appropriate row and actuates the "Modify Row" soft function key F12. In this regard, the program advances from decision instruction 1014 to decision instruction 1015, which determines whether the user desires to store the new row information. If not, the program goes to a decision instruction 1016 which determines whether the user has actuated the modify row soft function key F3.

If the user has not actuated the modify row soft function key, the program returns to the decision instruction 1012 and proceeds as described previously.

At decision instruction 1014, if the user has not actuated the "Done" soft function key F3, the program goes directly to the decision instruction 1016 and proceeds as described previously.

At decision instruction 1016, if it is determined the user has actuated the "modify row" soft function key F12, the program advances to a call command 1018 which causes the modify subroutine 1200 to be called. The modify subroutine 1200 will be described hereinafter. After the modify subroutine 1200 is executed, the program returns to the decision command 1012 and proceeds as described previously.

If at decision instruction 1015 a determination is made that the user has actuated the "Store" soft function key F8, the program goes to an exit command 1019 returning the program to the CRITICAL CARE subroutine 500 at decision instruction 513.

3. Modify Row

Considering now the MODIFY subroutine 1200 (FIG. 12) in greater detail, the modify subroutine begins in a start command 1201 whenever the user positions the cursor on an unstored row and activates a modify row function key such as key F12. In this regard, in a text box or cell, care path assessment or user defined section, only the name, comment, D/C time and/or frequency of an unstored row can be modified.

The MODIFY subroutine advances from the start command 1201 to a decision instruction 1203 which determines whether the user has highlighted one of the modify row options displayed in the modify row window (not shown). More particularly, to change the name, comment, discontinue time, or frequency, the user must select an edit labels option in the displayed window. To remove an unstored row, the user must select a delete row option in the displayed window. The user makes such selections by using the Up arrow and/or Down arrow keys and activating the enter key when the desired selection is highlighted. In this regard, if the user selects the delete row option, the program advances from the decision instruction 1203 to a return instruction 1205 which returns the program to the start command 1100 in the add row subroutine 1100 which simultaneously deletes the information entered by the user for the new row. In this regard, when the user subsequently activates the store function key, it should be understood the selected unstored row will not be stored. Instead, the row information previously entered will be deleted.

If at decision instruction 1203 the user does not activate the delete row option function key, the program advances to a decision instruction 1207 which determines whether the user desires to edit a screen label. If not, the program proceeds to the decision instruction 1203 and proceeds as described previously.

If the user desires to modify a label by selecting the edit label option, the program advances to a decision instruction 1209 which determines whether the user has completed editing the label. If not, the program loops at instruction 1209.

When the user selects the edit label option, an edit label window 2000 (FIG. 20) appears. After the user enters the requested data in the edit label window, the program goes to a return command 1211 which returns the program to the ADD NEW ROW subroutine 1100.

Considering now the EDIT TEXT CELL subroutine 1300 in greater detail, the EDIT TEXT CELL subroutine 1300 begins in a start instruction 1301. In this regard, all text cells can be edited for custom diagnoses on a per patient basis.

From the start instruction 1301, which is entered from the call command 516 in the CRITICAL CARE PATH subroutine 500, the program advances to a decision instruction 1303 which determines whether the user has selected a CRITICAL CARE PATH SCREEN such as the screen 1460. If not, the program loops at instruction 1303 until the user has completed selection of a desired screen. The user then moves the cursor to highlight a desired text cell and actuates a desired one of the edit text cell function keys. In this regard, the user either actuates an edit one cell soft function key F 9 or an edit all cells function key F10.

A decision instruction 1305 determines whether the user desires to edit one cell. If not, the program advances to a decision instruction 1307 which determines whether the user desires to edit all the cells in the selected screen. In this regard, when the user depresses either the edit one cell function key or the edit all cells function key, the program will advance from the instruction 1305 to a command instruction 1309 or from the decision instruction 1307 to a command instruction 1312.

Command instruction 1309 causes the selected text cell, to appear. The user then may edit the cell by typing in the desired edits in free text via the keyboard 24. In this regard, words are automatically wrapped to the next line of text while edits are performed in an insert mode. Utilization of the home, end, paper up, page down, insert and backspace function keys allow the user to edit the text in a highly efficient manner. The user may remove text in the selected text cell by actuating the "clear text" soft function key F5.

The program then advances to a decision instruction 1313 which determines whether the user has actuated the clear text function key which causes the program to advance from the decision instruction 1313 to a command instruction 1317 which in turn causes the text in the selected cell to be deleted. From instruction 1317 the program advances to a command instruction 1319 which causes any text entered in the box to be indicative of edited text. In this regard, the text that is edited will be underlined.

At decision instruction 1313, if the user does not desire to remove the text in a cell, the program advances directly to the command instruction 1319 which causes any edited text entered by the user to be underlined.

Next, the program advances to a decision instruction 1321 which determines whether the edits entered by the user have been accepted. To facilitate acceptance of the edited text, the edited text will appear underlined until stored and the new text will be visible in the selected cell and/or on all subsequent, identical cells for the selected item.

If the user has selected or activated an accept soft function key F3 to accept the edits as entered, the program whether the user has activated the store function key. The edited text will appear underlined until stored. New text will appear in the box and in all selected cells. If the user has not selected the accept function key, the program loops at instruction 1321.

If the user has not selected the store function key F8 at instruction 1323, the program loops at instruction 1325. When the primary cell store function key is selected, the program advances to a decision command 1325 which determines whether the user desires to view the edit history for the text window. If so, the program goes to a command instruction 1327 which causes the edited text in a cell to appear in reverse video when stored. The program then goes to an exit command 1329.

If the user did not desire to view the edit history, the program advances directly to the exit command 1329 which returns the program to the CRITICAL CARE subroutine 500.

If the user selects the edit all Cells function key, the program advances from instruction 1307 to command instruction 1312, which causes the selected primary cell and the associated secondary or repeat cells text to appear. The user may then edit the cell.

If the user desires to delete a primary text cell so it becomes a secondary or repeat cell, the user selects a delete cell soft function key. The program advances from decision instruction 1320 to command instruction 1322, which causes the text in the cell to appear in an offset color, such as a gray color, and then repeats the text from the previous primary cell into all the repeating cells thereafter. In this regard, the old primary cell becomes a secondary cell.

If the user selects the edit function and activates the accept soft function key, and does not desire to change the primary cell to a secondary cell, the program advances to the decision instruction 1323 and proceeds as described previously. If not, the program loops at instruction 1323 until the user activates the store function key. When the user activates the store function key, the modified text will change in all repeat or secondary cells.

If the user desires to view this edit history for text windows, the user activates a describe item soft function key. This in turn will cause the edited text to appear in revere video.

Considering now the GENERAL CHARTING subroutine 900 in greater detail with reference to FIG. 9, the GENERAL subroutine 900 begins at a start instruction 901 which is initiated by the call command 308 (FIG. 3). Next, the program proceeds to a decision instruction 903 which determines whether a system user desires to review a given flow sheet. If so, the program advances to a call instruction 904 which causes a FLOWSHEET REVIEW subroutine 700 (FIG. 7) to be executed. After the FLOWSHEET REVIEW subroutine 700 is executed, the program advances to a decision instruction 905. The FLOWSHEET REVIEW subroutine 700 is beyond the scope of the present invention and will not be described in greater detail.

At decision instruction 903, if it is determined the system user does not want to review any given flowsheet, the program advances to the decision instruction 905 which determines whether the system user desires to configure a flowsheet. If so, the program goes to a call instruction 906 which causes a CONFIGURE FLOWSHEET subroutine to be executed. The CONFIGURE FLOWSHEET subroutine is beyond the scope of the present invention and will not be described hereinafter in greater detail. It should be noted however, that each flowsheet can be configured with seven general functions and two specific functions as illustrated in Table I.

TABLE I

| FLOWSHEET RECONFIGURATION FUNCTIONS | |
| --- | --- |
| GENERAL FUNCTIONS | SPECIAL FUNCTIONS |
| Read Monitor | Add Row |
| Copy Forward | Modify Row |

TABLE I-continued

FLOWSHEET RECONFIGURATION FUNCTIONS

| GENERAL FUNCTIONS | SPECIAL FUNCTIONS |
|---|---|
| | D/C |
| | Describe Item |
| | Set Frequency |
| | Reset Schedule |
| | Annotation |

After the CONFIGURE FLOWCHART subroutine has been executed, the program goes to a decision instruction 907 which determines whether any other general flowsheet functions are required. If so, the program returns to decision instruction 903 and proceeds as described previously.

At decision instruction 905, if it is determined that the system user does not desire to configure another flowsheet, the program advances to the decision instruction 907. In this regard, at decision instruction 907 if it is determined that no other general flowsheet functions are necessary, the program advances to an exit command 909 which returns the program to the appropriate subroutine that initiated the call command. For example, the CHART subroutine 300 at decision instruction 309. The program proceeds from decision instruction 309 as described previously.

4. Discontinue Row

Figure 11:
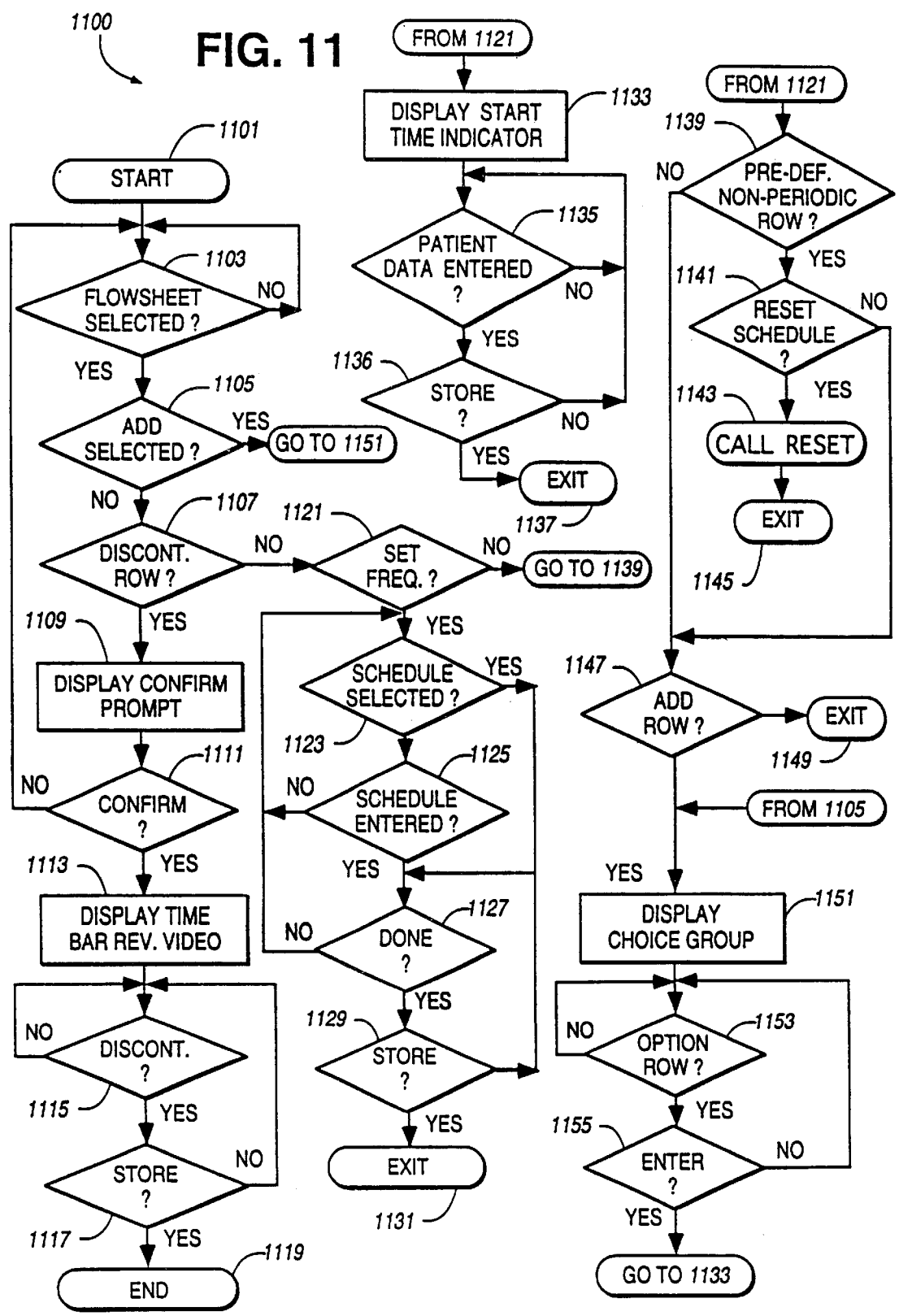
Figure 12:
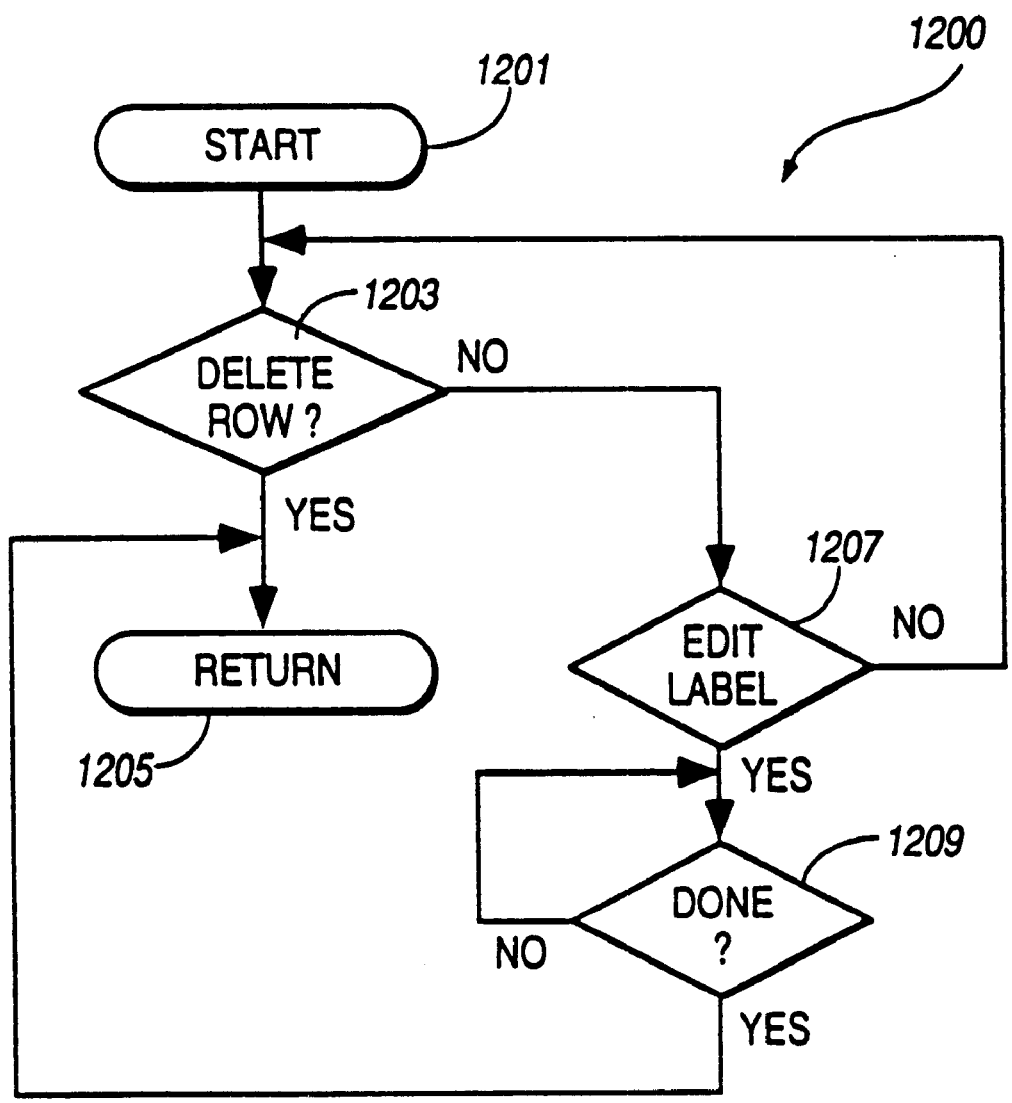
Figure 13:
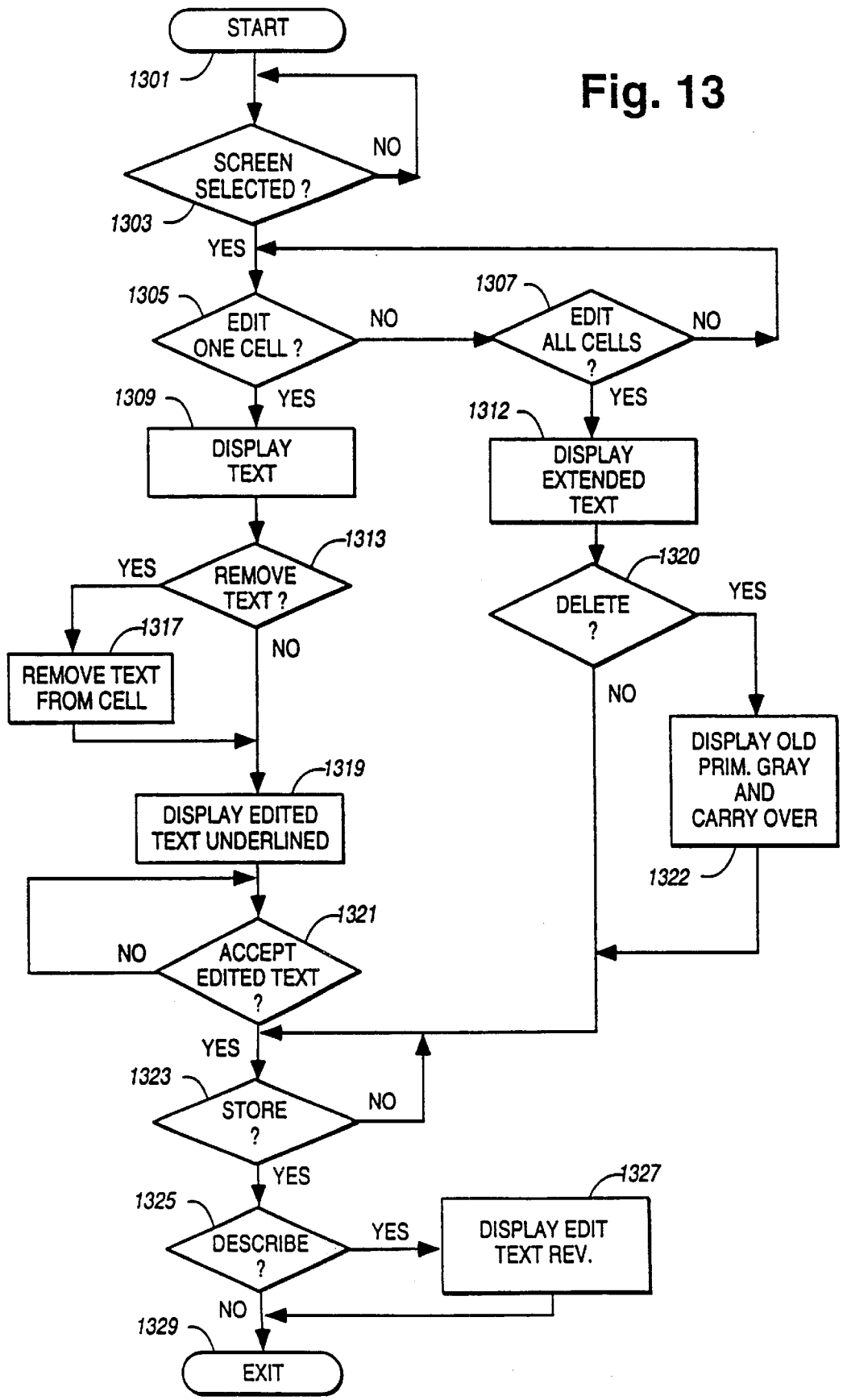

Considering now the DISCONTINUE ROW SUBROUTINE 1100 in greater detail with reference to FIG. 11, the DISCONTINUE ROW SUBROUTINE 1100 begins at a start instruction 1101 when the user desires to discontinue a row in a CRITICAL CARE PATH FLOWSHEET. In this regard, the program advances to a decision instruction 1103 which determines whether the user has selected a CRITICAL CARE PATH FLOWSHEET. If not, the program loops at instruction 1103 until the user selects a flowsheet.

When the user selects a flowsheet, the program proceeds to a decision instruction 1105 which determines whether the user has selected a desired data cell row to be added. In this regard, the user moves the cursor to the desired data cell and activates the new row function key.

If the user has selected to add a new row, the program goes to a command 1151 which displays a choice group. If not, the program advances to a decision instruction 1107 which determines whether the user desires to discontinue a desired row and time column. In this regard, the user moves the screen cursor to highlight the desired row and the time column and then activated the discontinue soft function key F5. If so, the program proceeds to a command instruction 1109 which causes the monitor 25 to display a confirmation prompt.

Next, the program advances to a decision instruction 1111 which determines if the user has entered via the keyboard 44 the letter "Y" for Yes to discontinue the flowsheet row or the letter "N" to abort the discontinue of the flowsheet row.

If the user enters the letter "N" the program returns to the decision instruction 1103 and proceeds as described previously. If the user enters the letter "Y" the program advances to a command instruction 1113 which causes a time bar and arrowhead to appear up to the time column where the cursor was positioned. In this regard, the time bar will appear black until the screen is stored.

If the user desires to remove a discontinue error, the user moves the cursor to the desired data cell within the selected row and activates the discontinue soft function key F5 again. The program advances from instruction 1113 to a decision instruction 1115 to make this determination. From decision box 1115 the program goes to a decision instruction 1117 which determines if the user has activated the "store" soft function key F8. If not, the program returns to decision box 1115 and proceeds as described previously. If so, the program goes to an exit command 1119.

If the user does not desire to discontinue a row, the program proceeds to a decision instruction 1121 to determine whether the user desires to set a frequency in a scheduled treatment. If so, the program advances to a decision instruction 1123 which determines whether the user has selected a schedule. The procedure for setting a frequency will be described hereinafter in greater detail.

If the user does not desire o set a frequently, the program advances to a decision instruction 1139 which determines whether the selected row is a predefined non-periodic row. If so, the program proceeds to a decision instruction to a decision instruction 1141 which determines if the user desires to reset the schedule in the selected row.

If at decision instruction 1139 it is determined the row is not a predefined non-periodic row, the program proceeds to a decision instruction 1147 which determines if the user desires to add a new predefined row. If not, the program advances to an exit command 1149.

Figure 22:
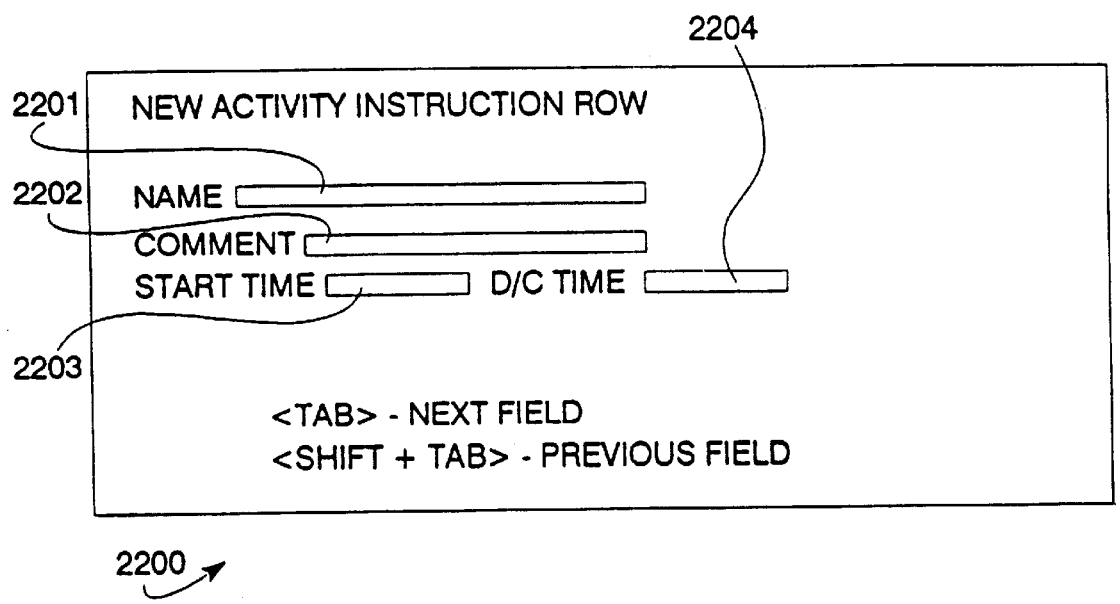
FIG. 22 is an add new row window generated by the system of FIG. 1.

If the user has indicated a desire to add a new row by activating a new row function key, such as a function key F3, the program goes to the command instruction 1151 which causes a NEW ROW SCREEN 2200 (FIG. 22) having an add group choice list with predefined groups to be displayed for the selected section type. As best seen in FIG. 22, the NEW ROW SCREEN 2200 includes a predefined a name area 2201, a predefined comment area 2202, a predefined start time area 2203 and a predefined discontinue (D/C) area 2204, where such predefined area includes a customization area for displaying the instruction entered by the user. The NEW ROW SCREEN 2200 provides the user with instructions for field movement within the screen. For example, by activating the tab key on the keyboard 44, the next field in the screen 2200 will be highlighted for receiving the date to be entered by the user. If, the user activates a shift key in combination with the tab key, the previous field in the screen 2200 will be highlighted.

After the choice group is displayed in the NEW ROW SCREEN 2200, the program proceeds to a decision instruction 1153 to determine if the user has made an option selection for the row. If not, the program loops at instruction 1153 until the user selects an option.

After the user selects an option, the program goes to a decision instruction 1155 which determines if the user has selected a desired row label and activated an enter function key. In this regard, when the enter key is activated, the selected row label will appear on the flowsheet screen and a start time indicator will also automatically appear on the screen for the selected row. Thus, the program advances from the decision instruction 1155 to the command instruction 1133 to cause the aforesaid display If the user does not activate the enter key, the program returns to instruction 1153 and proceeds as described previously.

From instruction 1133,the program advances to a decision instruction 1135 which determines if the user has entered the patient data for the new row. If not, the program loops at instruction 1135.

When the user has completed entry of the patient data, the program goes to the decision instruction 1136 which determines whether the user has stored the added row. If not, the program goes to the decision instruction 1135 and proceeds as described previously.

If the user has activated a store function key, the program goes from the decision instruction 1136 to an exit command 1137 terminating the add row subroutine.

From the foregoing, it should be understood the system 10 can also perform other functions such as the discontinuing of a row, setting a frequency in a selected schedule, resetting a schedule in a predefined non-periodic row and adding a non-periodic row.

The user can abort the new row mode by activating the cancel all function key, such as the function 2210. Alternatively, the user can clear all fields in the NEW ROW SCREEN 2200 and return to the name field by activating the clear fields function key 2215. The user nay also clear the default time when in a time field by activating a clear time function key 2200. If so, the program advances to a decision instruction 1113 which determines whether the user desires the entered data to be stored.

At decision instruction 1121, if the user has activated the "Set Frequency" soft function key F9, the program advances to a decision instruction 1123 to verify the user has selected a desired flowsheet and has highlighted the desired flowsheet row and time column. In this regard user types in the number corresponding to the desired. schedule.

If the user has not selected the schedule, the program goes to a decision instruction 1127 which determines whether the user has activated the done soft function key. If not, the program returns to the decision instruction 1123.and proceeds as described previously. If the user has selected a schedule, the program goes to decision instruction 1125 which determines whether,the choice number has been entered. If not, the program goes to decision instruction 1123 and proceeds as described previously and if so, the program goes to decision instruction 1127.

At decision instruction 1127, if the user has activated the done soft function key, the program advances to a decision instruction 1129, which determines whether the user hag activated the store soft function key. If not, the program returns to the decision instruction 1127 and proceeds as described previously. If so, the program goes to an exit command 1131.

5. Create Care Path Configuration

Considering now the creation of the care path database configuration data in greater detail, a new care path can be created and added to the user choice list for selection at any time. However, the adding of or creating of a care path for the database is restricted to designated users only.

In order to create a care path for the database, the designated user enters the name or other identifying information of a fictitious patient and then selects the care path screen by actuating the soft function key F11. A fictitious patient is identified, because there will be no actual care path, which will be retrieved. Thus, the care path screen will contain only blank entries so that the new care path can be created.

When the care path screen appears, such as the care path screen 1500 (FIG. 15), the designated user actuates the add care path function by causing the screen cursor to be positioned to active care paths section of the screen, such as section 1501, and then actuates the add care path function by actuating the soft function key F3.

When the soft function key F3 is actuated, a select care path type window appears, such as a window 1453 (FIG. 14C). The designated user then selects the care path type and depresses the enter key on the keyboard.

Upon depressing the enter key, and add care path window, such as an add care path window 1484 (FIG. 14E) will appear on the screen of the monitor. The designated user then enters in a desired care path name in free text, a start time and a post op time or a stabilization time if required for the desired type. It should be noted that the post-op and stabilization times must be entered. However, these entries will not be saved as part of the configuration database. In this regard, only relative time differences will be saved as part of the configuration.

When the designated user has finished entry of the. information in the care path window, the user actuates the done soft function key F3 which in turn causes the critical care path flowsheet screen to appear on the screen using the new row soft function key F3, edit one cell soft function key F9, edit all cells soft function key F10, discharge/expected outcome soft function key F11, set. schedule soft function key F4 and the set frequency soft function key F5, the designated user types in the care path information.

After all the care path information has been entered, the designated user causes the screen cursor to be positioned to the active care paths section and depresses the soft function key F12 to cause a default care path window 1498 (FIG. 14F) to appear on the screen of the monitor.

The user then enters the name of the desired care path in free text as it will appear on the choice list. Alternately, the designated user can press the enter key on the keyboard 44 to use the default care path name as displayed. If the default care path name is used, the existing care path will be replaced with the contents of the screen.

The designated user then depresses the enter key which in turn causes an identification prompt to appear on the screen of the monitor. The designated user then enters his or her identification code and actuates the enter key on the keyboard.

If the user has an authorized identification code, a configuration prompt 1499 (FIG. 14G) will appear on the screen with the new care path name. This name will be added to the choice list for the applicable care path type when the designated user subsequently depresses any key to complete the creation of the new care path in the database.

6. Modify Care Path Configuration

Considering now the modifying of the care path database configuration data in greater detail, an existing care path can be modified at any time. For example, through experience, it may be determined that a particular deviation in an existing care path occurs so frequently that a modified standard evolves over a period of time. When such an event occurs, the designated user can modify an existing care path. In this regard, the designated user follows a similar procedures as set forth herein for creating a new care path. The user modifies the current database configuration in substantially the same manner as creating database information.

Initially, the name or other identifying information of an actual patient is entered so that the care path to be modified will be retrieved. The remaining steps of the procedure are the same as the procedure of establishing a new care path.

After the entry of the patient identifying information, the designated user selects the critical care path screen by actuating the function key F11. Next, the user positions the cursor on the "active care path" section of the screen and actuates the function key F4 to set post-op times or stabilization times if they are not already set.

After setting the post-op time the user edits the care path as needed.

After the designated user has modified the care path screen information, the user actuates the soft function key F12 which in turn causes the default fault care path window to appear such as the window 1498. The user then enters the default care path name which in turn causes the existing care path information to be replaced with the modified information appearing on the screen of the monitor. The process is then completed in the same manner as described for creating a database care path configuration.

While particular embodiments of the present invention have been disclosed, it is to be understood that various different modifications are possible and are contemplated within the true spirit and scope of the appended claims. For example, there are a large number of equivalent devices and equipment which can be substituted for the preferred devices and equipment such as the keyboards, monitors and other such apparatus. Also, some portions or all of the preferred software implemented features can be implemented entirely in hardware logic circuits. There is no intention, therefore, of limitations to the exact abstract or disclosure herein presented.

What is claimed is:

1. A system for facilitating the management of the care of a group of patients by a health care provider, comprising:

a central computer for storing critical care information for a plurality of different patient diagnoses for different maladies for a given patient;

remote computers means coupled to said central computer for creating and storing a first active care path information corresponding to a specific one of said patient diagnoses for a given one of said patients;

said remote computers for creating and storing a second active care path information corresponding to a different specific one of said patient diagnoses for said given one of the patients;

said central computer being responsive to said remote computers means for causing said first active care path information to be added to said second active care path information to establish a customized critical care information for the given patient and for causing the customized multiple customized diagnoses critical care information to be stored to enable said customized critical care information to be retrieved by said remote computer to facilitate patient care management; and means for arranging said first and said second active care path information adjacent to one another to facilitate determining potential conflicts between said first active care path information and said second active care path information for said given patient;

wherein said first active care path information and said second active care path information are presented adjacent to one another when said customized critical care information for said given patient is retrieved by said remote computers means for enabling the health care provider to adjust said customized multiple diagnoses critical care information for resolving any potential conflicts so that a customized multiple diagnoses treatment information can then be entered and stored for a given patient.

2. A system according to claim 1, further having bedside units including a bedside computer for retrieving the customized critical care information of the given patient, and including a data entry device for entry of patient information in accordance with said first active care path information and said second active care path information of the customized critical care information.

3. A system according to claim 1, wherein said central computer means includes:

processor means for selectively adding sad first active care path information to said second active care path information; and algorithm means for enabling the user to adjust the customized critical care information to eliminate each determined conflict.

4. A system according to claim 2, wherein said remote computer means includes:

a processor for permitting a user to analyze each of the potential conflicts to determine if a conflict in patient treatment actually exists.

5. A system according to claim 4, further comprising:

means for displaying selectively patient treatment information for the retrieved care path information.

6. A system according to claim 5, wherein said central computer means further includes:

order means for arranging said first active care path information and said second active care path information in a time ordered sequence;

wherein said first active care path information and said second active care path information have associated expected outcomes; and means for causing each of the expected outcomes to be displayed in said time ordered sequence.

7. A system according to claim 6, wherein said order means includes:

series means for arranging the stored customized critical care information in a plurality of predefined groups, said predefined groups each being arranged in a series of rows and columns in said time ordered sequence.

8. A system according to claim 7, wherein said central computer further includes:

information means for retrieving the stored customized critical care information for a user selected individual one of said plurality of predefined groups; and means for further customizing the retrieved individual ones of the plurality of predefined groups in said time ordered sequence relative to the response of the given patient to treatment.

9. A system according to claim 8, wherein said means for further customizing includes:

sequence means for causing customized patient information to be entered at a given time in said time ordered sequence.

10. A system according to claim 9, further comprising:

means for enabling the user to determine whether the entered customized patient information should be repeated continuously in said time ordered sequence; and means for repeating the customized patient information at a user defined frequency in said time ordered sequence.

11. A system according to claim 10, wherein said means for repeating in response to the user can cause said repeated information to be discontinued anywhere in said time order sequence.

12. A system according to claim 1, wherein said first active care path information and said second active care path information include text information, and further including sorting means for arranging alphabetically said text information for said first active care path information and said second active care path information to facilitate identifying said potential conflicts.

13. A system according to claim 12, wherein text information is positioned adjacent to similar text information.

14. A system according to claim 1, wherein said critical care information includes assessment information.

15. A system according to claim 14, further including means for eliminating redundant assessment information when said one active care path information is added to said another active care path information.

16. A method of using a system for facilitating the management of the care of a group of patients by a health care provider, comprising:

storing critical care information for a plurality of patient diagnoses corresponding to different maladies for a given patient;

creating a first active care path information corresponding to a specific one of said patient diagnoses for a given one of said patients;

storing said first active care path information;

creating a second active are path information corresponding to another specific one of said patient diagnoses corresponding to a different malady for said given patient;

storing said second active care path information;

adding said first active care path information to said second active care path information to establish a customized multiple diagnosis critical care information for the given patient;

storing the customized multiple diagnosis critical care information;

arranging said first and second active care path information adjacent to one another for said given patient to facilitate determining potential conflicts between said first active care path information and said second active care path information; and presenting said first active care path information adjacent to said second active care path information for said given patient for enabling the health care provider to adjust said customized multiple diagnosis critical care path information for resolving said potential conflicts.

17. A method according to claim 16, further comprising:

retrieving the customized critical care information and adding patient information to said customized critical care information.

18. A method according to claim 16, wherein the step of adding includes:

displaying selectively patient treatment information for the retrieved care path information;

adding selectively the retrieved care path information where potential conflicts between the predefined standards of care exist;

permitting a user to analyze each of the potential conflicts to determine if a conflict in patient treatment actually exists; and enabling the user to customize the care path information to eliminate each determined conflict.

19. A method according to claim 18, wherein the step of displaying includes:

displaying each of a predefined standard of care treatments in a time ordered sequence; and displaying each of expected outcomes resulting from the predefined standard of care treatments in said time ordered sequence.

20. A method according to claim 19, further comprising:

arranging the stored customized critical care information in a plurality of predefined groups, said groups each being arranged in a series of rows and columns in said time ordered sequence.

21. A method according to claim 20, further comprising:

retrieving the stored customized critical care information for a user selected individual one of said plurality of predefined groups;

further customizing the retrieved individual ones of the plurality of predefined groups in said time ordered sequence relative to the response of the patient to treatment.

22. A method according to claim 21, wherein in the step of further customizing includes entering the customized information at a given time in said time ordered sequence.

23. A method according to claim 22, further comprising:

enabling the user to determine whether the entered customized information should be repeated continuously in said time ordered sequence; and repeating the customized information at a user defined frequency in said time ordered sequence.

24. A method according to claim 23 wherein said step of repeating can be discontinued anywhere in said time ordered sequence at the discretion of the user.

25. A method according to claim 20, wherein each row and column intersect to define a series of data information cells arranged in said time ordered sequence.

26. A method according to claim 25, wherein a user can customize the data information in any one of the cells.

27. A method according to claim 26, wherein the customized information entered into one cell in a given row is repeated for all the remaining cells occurring thereafter in said time ordered sequence.

28. A method according to claim 27, wherein the initial cell customized with customized information is a primary cell.

29. A method according to claim 25, wherein the primary cell includes indicia to indicate that said primary cell is a primary cell.

30. A method according to claim 27, wherein the information in the remaining cells occurring thereafter in said time ordered sequence are secondary cells.

31. A method according to claim 30, wherein the user can customize an individual one of said secondary cells to transform said one of said secondary cells to said primary cell.

32. A method according to claim 30, wherein the user can discontinue the secondary cells anywhere in said time ordered sequence.

33. A method according to claim 16, further comprising:

storing a plurality of predefined critical care path standards for a plurality of different types and kinds of medical surgical diagnoses;

identifying a patient diagnosed as requiring treatment for at least two of said plurality of different types and kinds of medical surgical diagnoses;

retrieving the stored predefined critical care path standards for said at least two diagnoses;

comparing flowsheets for the retrieved predefined critical care path standards for possible conflicts;

combining the flowsheets for the retrieved predefined critical care path standards into a single flowsheet; and providing an indication that a conflict was determined, said indication being the absence of the conflicting standards from said single flowsheet.

34. A method according to claim 33, further comprising:

a providing a prompt that the conflicting standards have been deleted from said single flowsheet; and receiving a replacement order to update said single flowsheet with replacement information for the deleted standards.

35. A system for facilitating the management of the care of a group of patients, comprising:

a group of data acquisition bedside units for each being individually associated with the patients for gathering patient management information;

a central computer including a processor and a memory unit for receiving and storing the gathered patient management information;

a plurality of remote computers means remotely located relative to the group of patients for receiving and displaying patient management information for utilization by healthcare providers;

a data bus for interconnecting said bedside units, said central computer and said remote computers to enable them to communicate with one another interactively;

said central computer processor for creating critical care information for each one of a plurality of different patient diagnoses corresponding to different maladies for a given patient, said critical care information being indicative of expected outcomes resulting from predefined standard of care treatment plans to be administered to patient to be treated;

the central computer memory unit for storing the created critical care information for a multiple of patient diagnoses corresponding to said different maladies for the given patient;

said remote computer means for retrieving the stored multiple diagnoses critical care information selectively for a given one of the patients;

means for creating and storing a first active care path plan corresponding to one of said predefined treatment plans for one of the multiple diagnoses and for creating and storing a second active care path plan corresponding to another one of said predefined treatment plans for another one of the multiple diagnoses for treating said given patient;

means for adding said first active care path plan to said second active care path plan to form a customized multiple diagnoses critical care path plan; and means for displaying simultaneously said first active care path plan and said second active care path plan to facilitate determining potential conflicts between said first and second active care path plans for said customized multiple diagnoses critical care path plan for a given patient;

wherein said first active care path plan and said second active care path plan are presented simultaneously to enable said customized multiple diagnoses critical care path plan to be adjusted to resolved said conflicts by comparing said first and second plans.

36. A system for facilitating the management of the care of a group of patients according to claim 35, further comprising:

means for modifying the stored critical information for patients to be treated thereafter.

37. A system according to claim 36, further comprising:

means responsive to retrieved critical care information for modifying said retrieved critical care information for a given one of the patients.

38. A system according to claim 37, further comprising:

means responsive to the modified retrieved critical care Information for causing at least one customized flowsheet to be displayed to facilitate patient treatment for said given one of the patients.

* * * * *

UNITED STATES PATENT AND TRADEMARK OFFICE
CERTIFICATE OF CORRECTION

PATENT NO.   : 6,401,072 B1
DATED        : June 4, 2002
INVENTOR(S)  : Chris A. Haudenschild, Jean Francois Lancelot and Kristopher S. Urquhart It is certified that error appears in the above-identified patent and that said Letters Patent is hereby corrected as shown below:

<u>Title page,</u>
Item [73], Assignee, change "Clini Comp" to -- CliniComp --

<u>Column 31,</u>
Line 61, change "sad" to -- said --

<u>Column 33,</u>
Line 8, change "are" to -- care --

<u>Column 36,</u>
Line 25, change "Information" to -- information --

Signed and Sealed this

Twenty-third Day of July, 2002

Attest:

Attesting Officer

JAMES E. ROGAN
*Director of the United States Patent and Trademark Office*